(12) United States Patent
Lichtenstein et al.

(10) Patent No.: US 11,445,911 B2
(45) Date of Patent: Sep. 20, 2022

(54) SYSTEM FOR TREATING UNWANTED TISSUE

(71) Applicant: IKOMED Technologies Inc., Vancouver (CA)

(72) Inventors: Samuel Victor Lichtenstein, Vancouver (CA); Daniel Gelbart, Vancouver (CA); Eran Elizur, Vancouver (CA); Kevin James Cannons, Vancouver (CA)

(73) Assignee: Ikomed Technologies Inc., Vancouver (CA)

( * ) Notice: Subject to any disclaimer, the term of this patent is extended or adjusted under 35 U.S.C. 154(b) by 740 days.

(21) Appl. No.: 16/304,265

(22) PCT Filed: May 25, 2017

(86) PCT No.: PCT/CA2017/050635
§ 371 (c)(1),
(2) Date: Nov. 23, 2018

(87) PCT Pub. No.: WO2017/201625
PCT Pub. Date: Nov. 30, 2017

(65) Prior Publication Data
US 2019/0090928 A1  Mar. 28, 2019

Related U.S. Application Data

(60) Provisional application No. 62/468,869, filed on Mar. 8, 2017, provisional application No. 62/341,229, filed on May 25, 2016.

(51) Int. Cl.
*A61B 18/14* (2006.01)
*A61B 5/00* (2006.01)
(Continued)

(52) U.S. Cl.
CPC ............ *A61B 5/0036* (2018.08); *A61B 5/015* (2013.01); *A61B 5/4836* (2013.01);
(Continued)

(58) Field of Classification Search
CPC ..... A61B 5/0036; A61B 5/015; A61B 5/4836; A61B 18/14; A61B 18/082;
(Continued)

(56) References Cited

U.S. PATENT DOCUMENTS 2,249,935 A  7/1941 Birtcher
2,276,996 A  3/1942 Milinowski
(Continued)

FOREIGN PATENT DOCUMENTS

CN  103025262 A  4/2013
EP  2094207 B1  9/2015
(Continued)

OTHER PUBLICATIONS

P Gebhardt, FPGA-based RF interference reduction techniques for simultaneous PET-MRI, Apr. 6, 2016, IOP Publishing, vol. 61, pp. 3500-3526 (Year: 2016).*

*Primary Examiner* — Michael F Peffley
(74) *Attorney, Agent, or Firm* — Oyen Wiggs Green & Mutala LLP

(57) ABSTRACT

The invention may be applied to selectively heat a diseased area in the lung while minimizing heating to the healthy area and surrounding tissue. This can be done by exposing the lung to an electromagnetic field causing dielectric or eddy current heating. The invention is particularly useful for treating emphysema as the diseased areas in emphysema patients have reduced blood flow. The diseased area will heat up rapidly while the healthy tissue will be cooled by the blood flow. This is particularly effective for treating emphysema because of the low mass of the lungs and the high (Continued)

blood flow. To avoid heating of surrounding organs the direction of the electromagnetic energy may be switched in a way it always passes through lungs but only intermittently passes through adjacent organs.

20 Claims, 9 Drawing Sheets

(51) Int. Cl.
    *A61B 5/01*     (2006.01)
    *A61B 18/08*     (2006.01)
    *A61B 18/18*     (2006.01)
    *A61B 18/00*     (2006.01)

(52) U.S. Cl.
    CPC ............ *A61B 18/082* (2013.01); *A61B 18/14* (2013.01); *A61B 18/1815* (2013.01); *A61B 2018/00005* (2013.01); *A61B 2018/00541* (2013.01); *A61B 2018/00577* (2013.01); *A61B 2018/00642* (2013.01); *A61B 2018/00678* (2013.01); *A61B 2018/00708* (2013.01); *A61B 2018/00714* (2013.01); *A61B 2018/00791* (2013.01); *A61B 2018/00809* (2013.01); *A61B 2018/00815* (2013.01); *A61B 2018/00875* (2013.01); *A61B 2018/142* (2013.01)

(58) Field of Classification Search
    CPC ........... A61B 2018/00708; A61B 2018/00809; A61B 2018/00875; A61B 2018/00791; A61B 2018/00678; A61B 2018/142; A61B 2018/00005; A61B 2018/00714; A61B 18/1815; A61B 2018/00541; A61B 2018/00577; A61B 2018/00642; A61B 2018/00815; A61B 18/04
    USPC .......................................................... 606/33
    See application file for complete search history.

(56) References Cited

U.S. PATENT DOCUMENTS

| | | | |
|---|---|---|---|
| 2,549,399 A | | 4/1951 | Tawney |
| 3,638,657 A | | 2/1972 | Mettler |
| 3,747,013 A | | 7/1973 | Mettler |
| 3,800,802 A | | 4/1974 | Berry et al. |
| 4,269,199 A | * | 5/1981 | Armitage ................ A61N 5/01 607/154 |
| 4,305,115 A | | 12/1981 | Armitage |
| 4,798,215 A | | 1/1989 | Turner |
| 5,010,897 A | * | 4/1991 | Leveen .................. A61N 1/403 600/13 |
| 5,364,392 A | | 11/1994 | Warner et al. |
| 5,503,150 A | * | 4/1996 | Evans ....................... A61N 5/02 600/427 |
| 6,181,970 B1 | * | 1/2001 | Kasevich ............... A61B 18/18 607/101 |
| 6,312,426 B1 | * | 11/2001 | Goldberg et al. ...... A61B 18/04 606/33 |
| 6,330,479 B1 | * | 12/2001 | Stauffer .................. A61N 5/02 607/101 |
| 6,853,865 B2 | | 2/2005 | Beens et al. |
| 7,953,500 B2 | | 5/2011 | Bingham et al. |
| 7,979,139 B2 | | 7/2011 | Beens et al. |
| 8,444,635 B2 | * | 5/2013 | Lichtenstein ...... A61B 18/1815 606/33 |
| 8,467,858 B2 | | 6/2013 | Vertikov et al. |
| 8,585,645 B2 | | 11/2013 | Barry et al. |
| 9,028,482 B2 | | 5/2015 | Collins |
| 9,113,858 B2 | | 8/2015 | Barry et al. |
| 9,192,422 B2 | | 11/2015 | Collins |
| 9,962,225 B2 | * | 5/2018 | McMillan ............... A61B 18/20 |
| 10,953,235 B2 | * | 3/2021 | Anderson et al. ..... A61B 18/10 |
| 2008/0154252 A1 | * | 6/2008 | Torchia .................. A61B 18/28 606/13 |
| 2011/0054431 A1 | * | 3/2011 | Turnquist ............... A61B 5/201 604/385.01 |
| 2011/0060393 A1 | * | 3/2011 | Azure ................ A61B 18/1206 607/115 |
| 2011/0301450 A1 | * | 12/2011 | Hue et al. ............. A61B 5/055 600/411 |
| 2013/0116679 A1 | | 5/2013 | Van Der Weide et al. |
| 2013/0261621 A1 | * | 10/2013 | Kramer .................. A61B 18/08 606/42 |
| 2015/0018817 A1 | * | 1/2015 | Willard .................... B29C 48/10 606/41 |
| 2016/0184013 A1 | | 6/2016 | Brannan et al. |
| 2017/0143414 A1 | * | 5/2017 | Sliwa .................. A61B 18/1492 |
| 2018/0000533 A1 | | 1/2018 | Boll et al. |
| 2018/0015294 A1 | * | 1/2018 | Anderson, Jr. et al. . A61N 1/40 |
| 2019/0030356 A1 | * | 1/2019 | Schwarz ................ A61N 2/002 |

FOREIGN PATENT DOCUMENTS

| | | | |
|---|---|---|---|
| KR | 10-2011-0026244 | * | 3/2011 |
| KR | 10-2011-0026244 A | | 3/2011 |
| KR | 10-1080603 B1 | | 11/2011 |
| WO | 03047603 A2 | | 6/2003 |
| WO | 2004022160 A1 | | 3/2004 |
| WO | 2016109437 A1 | | 7/2016 |
| WO | 2016119033 A2 | | 8/2016 |

* cited by examiner

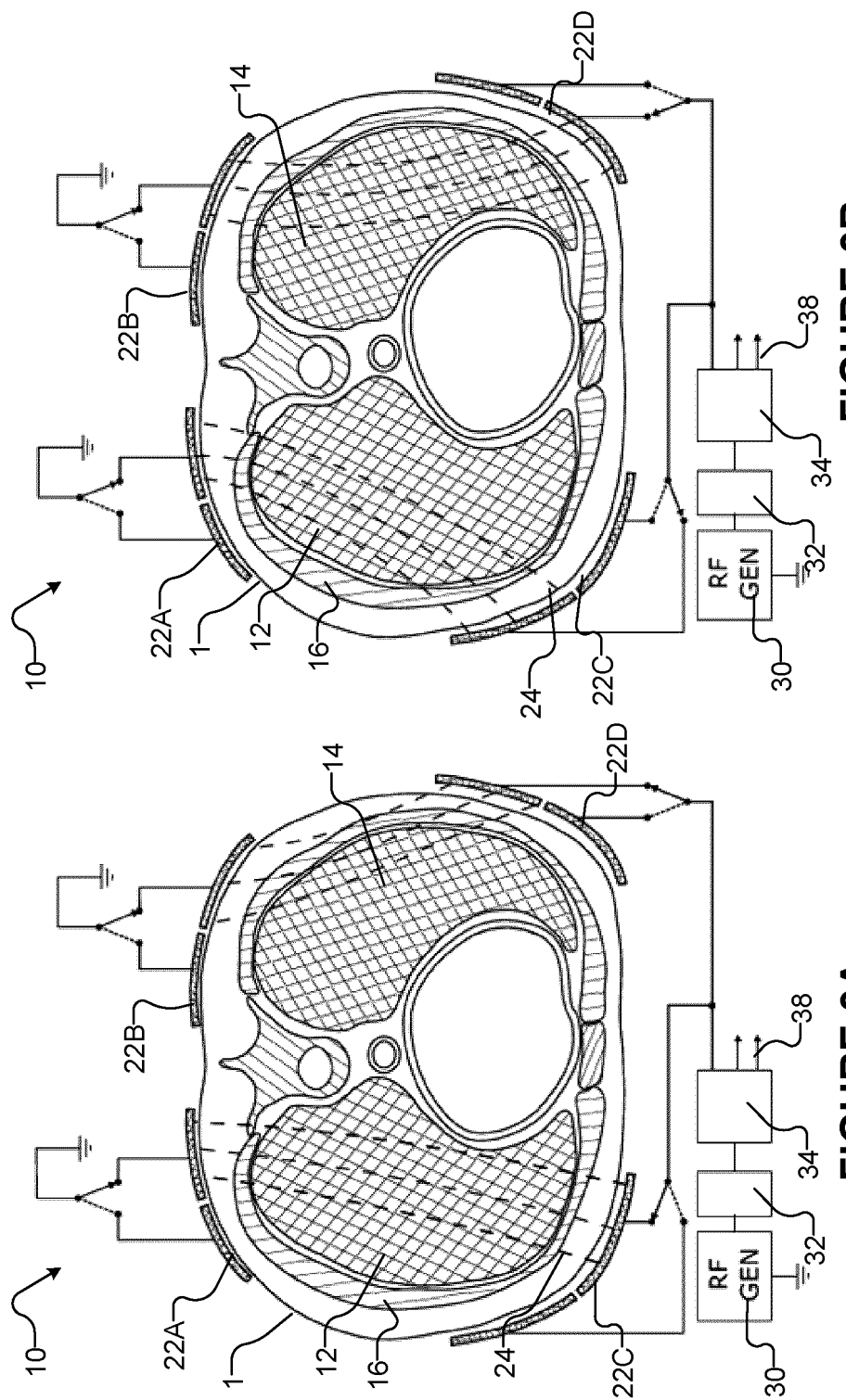

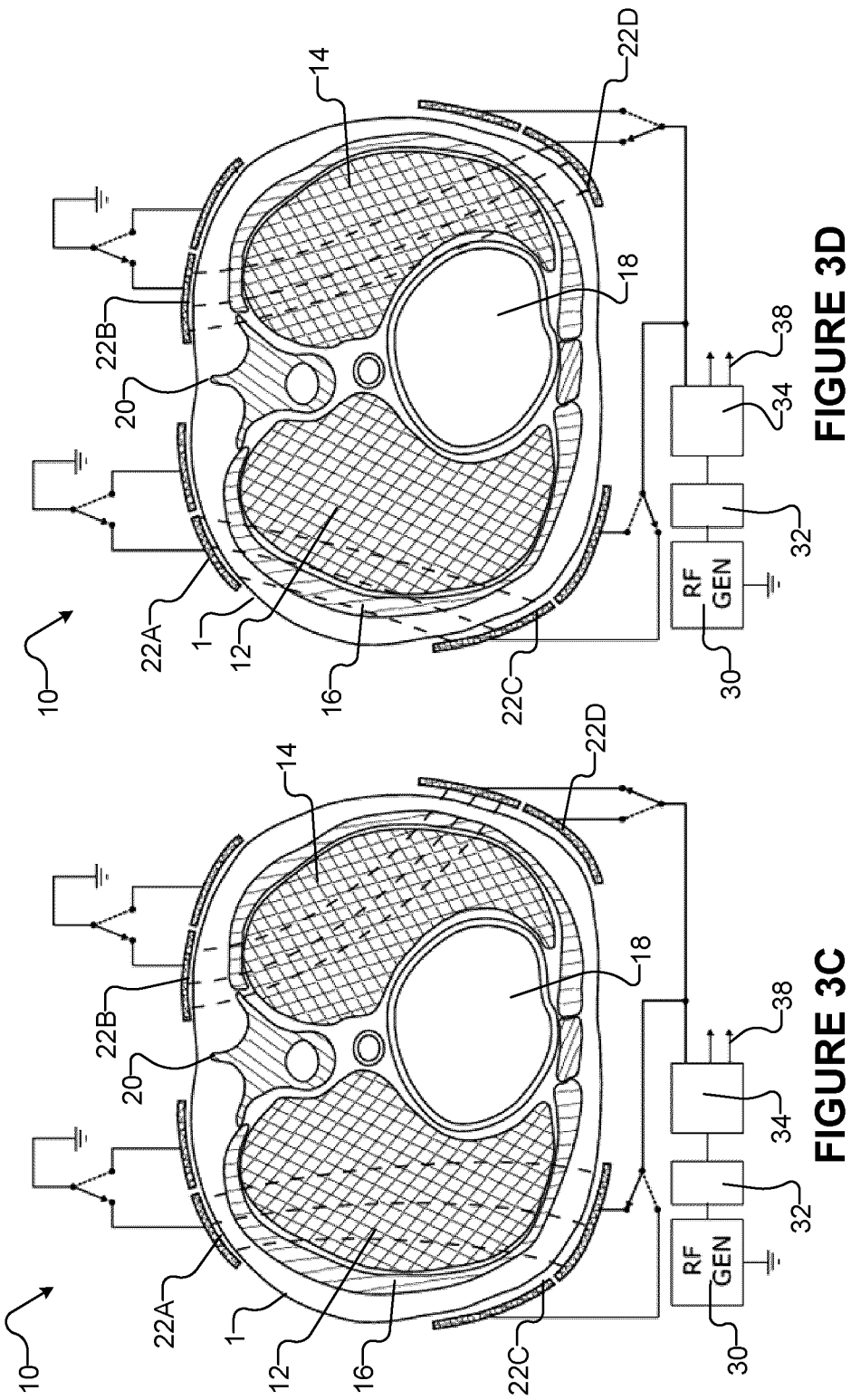

SYSTEM FOR TREATING UNWANTED TISSUE

CROSS-REFERENCE TO RELATED APPLICATIONS

This application claims priority from U.S. Application No. 62/341,229 filed 25 May 2016 and U.S. Application No. 62/468,869 filed 8 Mar. 2017. For purposes of the United States, this application claims the benefit under 35 U.S.C. § 119 of U.S. Application No. 62/341,229 filed 25 May 2016 entitled CLOSED LOOP CONTROL OF TREATMENT FOR EMPHYSEMA and U.S. Application No. 62/468,869 filed 8 Mar. 2017 entitled SYSTEM FOR TREATING UNWANTED TISSUE, each one of which is hereby incorporated herein by reference for all purposes.

FIELD

The invention relates to the medical field and in particular to the treatment of unwanted tissues. The invention has example application in treating lung diseases such as chronic obstructive pulmonary disease (COPD), one example of which is emphysema.

BACKGROUND

There are a variety of medical conditions for which treatment can beneficially include destroying or affecting a non-desired tissue. Such treatments should ideally avoid harming normal tissues adjacent to the non-desired tissue. For example, some lung conditions can benefit from treatments that involve destroying or affecting diseased lung tissue. Some of these treatments involve heating the lung tissue.

Background information on lung disease can be found in medical textbooks, such as "Pulmonary Pathophysiology" by Dr. John B. West, ISBN 0-683-08934-X. Emphysema is a disease that damages the alevioli (air sacs) in a patient's lungs. Affected air sacs can rupture. This alters the distribution of air spaces in the lungs and reduces the surface area of the lungs available to take up oxygen. The lung damage caused by emphysema can trap stale air in the lungs and reduce the flow of fresh, oxygen-rich air into the lungs. In a patient suffering from emphysema, diseased parts of the patient's lungs cannot easily ventilate through the bronchi and trachea, thus preventing the lungs from fully deflating and inflating. Air trapped inside the lungs can prevent the diaphragm from moving up and down naturally.

Some prior art approaches to heating diseased tissue within the lung involve inserting an ablation device through the trachea and bronchi into the diseased area (for example, see Brannan et al. US 2016/0184013). This approach has various shortcomings: only a small part of the lung is accessible, precise mapping of the diseased area is required, and the ablation device must be accurately guided to a precise location. It would be beneficial to provide a system that can automatically heat tissues in diseased areas without having to locate the diseased areas precisely. It would also be beneficial to be able to heat all diseased parts of the lung without excessively heating the healthy parts or the surrounding tissue.

Armitage, U.S. Pat. No. 4,269,199 discloses a method for inducing local hyperthermia in treatment of a tumor by short wave diathermy. The method involves moving an induction coil over the portion of the body containing the tumor such that the axis of the coil constantly transects different portions of the tumor.

Turner, U.S. Pat. No. 4,798,215 discloses a combined hyperthermia treatment and non-invasive thermometry apparatus.

Leveen, U.S. Pat. No. 5,010,897 discloses an apparatus for the deep heating of cancers. The apparatus employs two single turn coaxial coils which rotate synchronously in planes which are parallel to each other with the central axis of each coil lying in exactly the same line which is perpendicular to the plane of the coil. The summated magnetic field of the rotating coils continuously heats a tumor.

Evans, U.S. Pat. No. 5,503,150 discloses an apparatus and method for noninvasively locating and heating a volume of tissue that include the ability to detect temperature changes in the volume of tissue.

Kasevich, U.S. Pat. No. 6,181,970 discloses medical systems and instruments which utilize microwave energy to provide heat treatment and diagnostic imaging of tissue.

Barry et al., U.S. Pat. No. 8,585,645 discloses treating locations in a patient's lung using high temperature vapor delivered through the inner lumen of a catheter.

Turnquist et al., US2011/0054431 discloses devices and methods to non-invasively heat bodily tissues and fluid using emitted energy and non-invasively measure the resulting temperature changes in the target and surrounding fluid and tissue to detect and/or treat for various physical conditions, such as, for example, vesicoureteral reflux.

Lichtenstein et al., U.S. Pat. No. 8,444,635 which is hereby incorporated herein by reference discloses a system that exposes undesired tissue to a scanning focused microwave beam. U.S. Pat. No. 8,444,635 explains that the system is particularly useful for heating tissues in which the undesired tissue has reduced blood flow. The undesired tissues will heat up relatively rapidly while surrounding healthy tissues will be cooled by the blood flow. This differential heating effect is particularly strong in the lungs because healthy lung tissue has low density and high blood flow. U.S. Pat. No. 8,444,635 provides as an example application treating emphysema.

Vertikov et al., U.S. Pat. No. 8,467,858 describes devices and techniques for thermotherapy based on optical imaging.

There remains a need for apparatus and methods useful for controlling and/or delivering hyperthermy treatments.

SUMMARY

This invention has a number of aspects. These aspects include, without limitation:
  Apparatus useful for selectively heating tissues within a patient;
  Control systems for hyperthermy apparatus;
  Methods for controlling apparatus for selectively heating tissues within a patient;
  Methods for treating a patient which include selective heating of tissues within the patient.
An example and non-limiting application of methods and apparatus as described herein is treatment of diseased lung tissues, for example, lung tissues affected by emphysema or other forms of COPD.
  Innovations described herein include:
  Apparatus and methods useful in providing closed-loop control of temperature in tissues of a patient;
  Apparatus and methods useful for planning delivery of electromagnetic radiation to heat target tissues in a patient;

Apparatus and methods useful for heating tissues in patients with compensation and/or accommodation for differential perfusion;

Apparatus and methods useful for heating tissues in patients which include novel feature combinations;

Medical methods for treatment of emphysema and/or COPD.

These innovations may be applied individually or in any combinations.

Further aspects and example embodiments are illustrated in the accompanying drawings and/or described in the following description.

Enumerated Example Embodiments

The following enumerated example embodiments illustrate various non-limiting aspects of the invention.

1. Medical thermal ablation apparatus useful for treatment of emphysema or COPD, the apparatus comprising:
    a plurality of electromagnetic signal applicators, the plurality of electromagnetic signal applicators adapted to deliver electromagnetic energy to lung tissues for differential heating of diseased and healthier portions of the lung tissues, the plurality of electromagnetic signal applicators comprising a first set of two or more first electromagnetic signal applicators positionable on one side of a body to be treated and at a second set of at least one second electromagnetic signal applicators positionable on a second side of the body to be treated opposed to the first side such that the body is between the first and second electromagnetic signal applicators (or any other aspect herein) wherein the first and second electromagnetic signal applicators;
    a heating energy signal generator;
    a selector circuit connected to receive an output signal from the heating energy signal generator and to selectively apply the output signal between any of a plurality of pairs of the electromagnetic signal applicators, the pairs of the electromagnetic signal applicators each comprising one of the first electromagnetic signal applicators and one of the second electromagnetic signal applicators;
    a controller connected to control the selector circuit, the controller operable to switch from applying the output signal from a currently selected one of the pairs of electromagnetic signal applicators to a different one of the pairs of electromagnetic signal applicators at spaced apart times.

2. The medical thermal ablation apparatus according to aspect 1 (or any other aspect herein) (or any other aspect herein) wherein the electromagnetic signal applicators each comprises an electrode.

3. The medical thermal ablation apparatus according to aspect 2 (or any other aspect herein) comprising an impedance matching network between the heating energy signal generator and the electrodes.

4. The medical thermal ablation apparatus according to aspect 3 (or any other aspect herein) wherein the impedance matching network comprises a plurality of settings, each of the settings provides impedance matching for at least one of the plurality of pairs of electrodes, each of the pairs of electrodes correspond to one of the settings and the controller is connected to control the impedance matching network to switch the impedance matching network to the setting corresponding to the currently selected one of the pairs of electrodes.

5. The medical thermal ablation apparatus according to any one of aspects 2 to 4 (or any other aspect herein) wherein the controller is configured to switch from applying the output signal from the currently selected one of the pairs of electrodes to a different one of the pairs of electrodes at a frequency of 100 Hz or less.

6. The medical thermal ablation apparatus according to any one of aspects 2 to 5 (or any other aspect herein) wherein the electrode selector circuit comprises a first switch or network of switches switchable to connect a first output of the heat energy signal generator to one of the first electrodes.

7. The medical thermal ablation apparatus according to any one of aspects 2 to 6 (or any other aspect herein) wherein the second electrodes comprise a plurality of second electrodes and the electrode selector circuit comprises a second switch or network of switches switchable to connect a second output of the heat energy signal generator to one of the plurality of second electrodes.

8. The medical thermal ablation apparatus according to aspect 7 (or any other aspect herein) wherein one of the first and second outputs of the heat energy signal generator is a ground potential.

9. The medical thermal ablation apparatus according to any one of aspects 1 to 8 (or any other aspect herein) wherein the heating energy signal generator comprises a radiofrequency (RF) signal generator.

10. The medical thermal ablation apparatus according to aspect 9 (or any other aspect herein) wherein the RF signal generator is operable to output a signal having a frequency of at least 1 MHz.

11. The medical thermal ablation apparatus according to aspect 10 (or any other aspect herein) wherein the frequency is in the range of about 10 MHz to about 100 MHz.

12. The medical thermal ablation apparatus according to any one of aspects 1 to 11 (or any other aspect herein) (or any other aspect herein) wherein the controller is connected to receive a temperature signal indicative of a temperature of tissue at one or more locations within the body and is configured to apply feedback control to regulate heating energy delivered into the body from the heat energy signal generator based at least in part on the temperature signal.

13. The medical thermal ablation apparatus according to any one of aspects 1 to 12 (or any other aspect herein) (or any other aspect herein) wherein the controller is configured to apply time domain modulation to the output signal of the heat energy signal generator.

14. The medical thermal ablation apparatus according to any one of aspects 1 to 13 (or any other aspect herein) (or any other aspect herein) wherein the controller is configured to control the heat energy signal generator to emit the output signal as a pulsed signal and the controller is configured to control widths of the pulses.

15. The medical thermal ablation apparatus according to any one of aspects 12 to 14 (or any other aspect herein) further comprising a subcutaneous and/or invasive temperature sensor and the temperature signal comprises an output signal from the subcutaneous and/or invasive temperature sensor.

16. The medical thermal ablation apparatus according to aspect 15 (or any other aspect herein) wherein the subcutaneous and/or invasive temperature sensor comprises a thermistor.

17. The medical thermal ablation apparatus according to any one of aspects 12 to 16 (or any other aspect herein) wherein the controller comprises a thermal model of at least a portion of the body, the thermal model correlating temperature at one of the locations to temperature of a location of interest and the controller is configured to apply the thermal model using the temperature signal as an input and to regulate the heating energy based at least in part on an output of the thermal model.

18. The medical thermal ablation apparatus according to aspect 17 (or any other aspect herein) wherein the thermal model models comprise some or all of: thermal conductivities of different tissue types in the body, distributions of the different tissue types in the body, geometries of the electromagnetic energy applicators, and blood circulation in the body.

19. The medical thermal ablation apparatus according to any one of aspects 12 to 18 (or any other aspect herein) wherein the temperature signal is derived from a non-contact temperature measurement.

20. The medical thermal ablation apparatus according to any one of aspects 12 to 19 (or any other aspect herein) wherein the temperature signal comprises a signal derived from processing a magnetic resonance imaging (MRI) signal.

21. The medical thermal ablation apparatus according to any one of aspects 2 to 20 (or any other aspect herein) wherein the electrodes of at least one of the first and second sets of electromagnetic signal applicators are arranged in an array.

22. The medical thermal ablation apparatus according to aspect 21 (or any other aspect herein) wherein the array is shaped to generally conform with a projection of a lung within the body.

23. The medical thermal ablation apparatus according to aspect 21 or 22 (or any other aspect herein) wherein the array is a two-dimensional array.

24. The medical thermal ablation apparatus according to aspect 1 (or any other aspect herein) wherein the first and second sets of electromagnetic signal applicators respectively comprise first and second two-dimensional arrays of electrodes.

25. The medical thermal ablation apparatus according to aspect 24 (or any other aspect herein) wherein the two-dimensional arrays of electrodes are each made up of an equal number of electrodes.

26. The medical thermal ablation apparatus according to aspect 24 or 25 (or any other aspect herein) wherein each electrode of the first array of electrodes is positioned directly opposite a corresponding electrode of the second array of electrodes.

27. The medical thermal ablation apparatus according to any one of aspects 24 to 26 (or any other aspect herein) wherein the first array of electrodes comprises a first column of electrodes axially spaced apart along the body and a second column of electrodes axially spaced apart along the body.

28. The medical thermal ablation apparatus according to any one of aspects 24 to 27 (or any other aspect herein) wherein the first and second arrays of electrodes have configurations that are mirror images of one another.

29. The medical thermal ablation apparatus according to aspect 27 or 28 (or any other aspect herein) wherein each of the first and second columns of electrodes is made up of three to seven electrodes.

30. The medical thermal ablation apparatus according to any one of aspects 24 to 29 (or any other aspect herein) wherein the first array of electrodes comprises at least four columns of electrodes with the electrodes of each column of electrodes axially spaced apart along the body.

31. The medical thermal ablation apparatus according to any one of aspects 12 to 30 (or any other aspect herein) wherein the controller is configured to regulate the heating energy to raise a temperature at one of the one or more locations to a temperature of at least 50 C and to maintain the temperature at 50 C or higher for a selected time period.

32. The medical thermal ablation apparatus according to any one of aspects 12 to 31 (or any other aspect herein) wherein the controller is configured to regulate the heating energy to prevent the temperature at one of the one or more locations from exceeding a safe temperature threshold.

33. The medical thermal ablation apparatus according to aspect 32 (or any other aspect herein) wherein the safe temperature threshold is lower than 50 C.

34. The medical thermal ablation apparatus according to aspect 32 or 33 (or any other aspect herein) wherein the controller is configured to discontinue application of the heating energy if the temperature at the one location exceeds the safe temperature threshold.

35. The medical thermal ablation apparatus according to aspect 32 or 33 (or any other aspect herein) wherein the controller is configured to modulate application of heating energy from the heating energy signal generator if the temperature at the one location is rising toward the safe temperature threshold at a rate faster than a temperature rise threshold and/or is closer to the safe temperature threshold than a safety margin.

36. The medical thermal ablation apparatus according to any one of aspects 2 to 35 (or any other aspect herein) wherein the apparatus comprises shields located between one or more of the electrodes and the body.

37. The medical thermal ablation apparatus according to aspect 36 (or any other aspect herein) wherein the shields are movable relative to the electrodes.

38. The medical thermal ablation apparatus according to aspect 36 or 37 (or any other aspect herein) wherein the shields have a spatially-varying electrical impedance.

39. The medical thermal ablation apparatus according to any one of aspects 2 to 38 (or any other aspect herein) wherein the apparatus comprises a source of an electrically conductive fluid connected to supply the electrically conductive fluid to outlets at the electrodes.

40. The medical thermal ablation apparatus according to any one of aspects 2 to 39 (or any other aspect herein) wherein the electrodes of the first set of electromagnetic signal applicators are different in area from the electrodes of the second set of electromagnetic signal applicators.

41. The medical thermal ablation apparatus according to any one of aspects 2 to 40 (or any other aspect herein) wherein at least some of the electrodes comprise bladders connected to a supply of an electrically-conductive fluid.

42. The medical thermal ablation apparatus according to aspect 41 (or any other aspect herein) wherein the apparatus comprises one or more pumps connected to evacuate the electrically-conductive fluid and the controller is configured to operate the one or more pumps to evacuate the electrically-conductive fluid from one or more of the bladders, when the electrically conductive fluid has been evacuated from the one or more bladders operate a MRI machine to acquire MRI data from the body.

43. The medical thermal ablation apparatus according to aspect 42 (or any other aspect herein) wherein the controller is configured to process the MRI data to obtain information characterizing temperatures at one or more locations within the body.

44. The medical thermal ablation apparatus according to aspect 1 (or any other aspect herein) wherein the electromagnetic signal applicators each comprises a coil.

45. The medical thermal ablation apparatus according to any one of aspects 1 to 44 (or any other aspect herein) wherein the electromagnetic signal applicators are mounted to move relative to the body.

46. The medical thermal ablation apparatus according to any one of aspects 1 to 45 (or any other aspect herein) wherein the electromagnetic signal applicators are mounted to a frame that is rotatable relative to the body and the apparatus comprises a motor connected to drive rotation of the frame.

47. The medical thermal ablation apparatus according to aspect 46 (or any other aspect herein) wherein the electromagnetic signal applicators are mounted for axial movement relative to the body and the apparatus comprises one or more actuators coupled to move the electromagnetic signal applicators axially while the frame is being rotated such that the electromagnetic signal applicators are moved helically relative to the body.

48. The medical thermal ablation apparatus according to any one of aspects 1 to 44 (or any other aspect herein) wherein at least one of the first and second electromagnetic signal applicators is stationary and the apparatus comprises an actuator controlled by the controller and operable to move the body relative to the at least one of the first and second electromagnetic signal applicators.

49. The medical thermal ablation apparatus according to any one of aspects 1 to 48 (or any other aspect herein) comprising bias means for biasing one or more of the electromagnetic signal applicators toward the body.

50. The medical thermal ablation apparatus according to aspect 49 (or any other aspect herein) wherein the bias means comprises an inflatable chamber.

51. The medical thermal ablation apparatus according to any one of aspects 49 to 50 (or any other aspect herein) wherein the one or more of the electromagnetic signal applicators is flexible and the bias means is adapted to flex the one or more of the electromagnetic signal applicators to conform to a concave surface.

52. The medical thermal ablation apparatus according to aspect 50 (or any other aspect herein) comprising a source of a pressurized cool fluid in fluid communication with the inflatable chamber.

53. Medical thermal ablation apparatus useful in the treatment of emphysema or COPD, the apparatus comprising:
  a heating energy signal generator;
  one or more electromagnetic energy signal applicators connected to receive an output signal from the heating energy signal generator and operative to couple electromagnetic energy from the signal generator into tissues of a body, the one or more electromagnetic energy signal applicators comprising one or more signal applicators selected from the group consisting of: electrodes; coils and antennas; and
  a controller connected to receive a connected to receive a temperature signal indicative of a temperature of the tissue at one or more locations within the body wherein the controller is configured to apply feedback control to regulate heating energy delivered into the body from the heat energy signal generator based at least in part on the temperature signal.

54. The medical thermal ablation apparatus according to aspect 53 (or any other aspect herein) wherein the controller is configured to apply time domain modulation to the heat energy signal generator.

55. The medical thermal ablation apparatus according to any one of aspects 53 to 54 (or any other aspect herein) wherein the controller is configured to control the heat energy signal generator to emit the output signal as a pulsed signal and the controller is configured to control widths of pulses in the pulsed signal.

56. The medical thermal ablation apparatus according to any one of aspects 53 to 55 (or any other aspect herein) further comprising a subcutaneous and/or invasive temperature sensor wherein the temperature signal comprises an output signal from the subcutaneous and/or invasive temperature sensor.

57. The medical thermal ablation apparatus according to aspect 56 (or any other aspect herein) wherein the subcutaneous and/or invasive temperature sensor comprises a thermistor.

58. The medical thermal ablation apparatus according to aspect 56 or 57 (or any other aspect herein) wherein the subcutaneous and/or invasive temperature sensor is deployed in a fine needle.

59. The medical thermal ablation apparatus according to any one of aspects 53 to 58 (or any other aspect herein) wherein the controller comprises a thermal model of at least a portion of the body, the thermal model correlating temperature at one of the locations to temperature of a location of interest and the controller is configured to apply the thermal model using the temperature signal as an input and to regulate the heating energy based at least in part on an output of the thermal model.

60. The medical thermal ablation apparatus according to aspect 59 (or any other aspect herein) wherein the thermal model comprises some or all of: thermal conductivities of different tissue types in the body, distributions of the different tissue types in the body, geometries of the electromagnetic energy applicators, and blood circulation in the body.

61. The medical thermal ablation apparatus according to any one of aspects 53 to 55 (or any other aspect herein) wherein the temperature signal is derived from a non-contact temperature measurement.

62. The medical thermal ablation apparatus according to aspect 61 (or any other aspect herein) wherein the temperature signal comprises a signal derived from processing a magnetic resonance imaging (MRI) signal.

63. The medical thermal ablation apparatus according to any one of aspects 53 to 62 (or any other aspect herein) wherein the one or more signal applicators are controllable to alter a direction of electrical fields and the controller is configured to periodically control the one or more signal applicators to alter the direction.

64. The medical thermal ablation apparatus according to aspect 63 (or any other aspect herein) wherein the signal applicator comprises an antenna and at least one actuator coupled to movably position the antenna (or any other aspect herein) wherein the controller is configured to move the antenna to alter the direction of the electrical fields.

65. The medical thermal ablation apparatus according to aspect 63 (or any other aspect herein) wherein the signal applicator comprises a plurality of pairs of electrodes and an electrode selector circuit and the controller is configured to operate the electrode selector circuit to apply an output of the heating energy signal generator across different ones of the pairs of electrodes at different times.

66. The medical thermal ablation apparatus according to aspect 63 (or any other aspect herein) wherein the signal applicator comprises at least one pair of electrodes and at least one actuator operable to move the at least one pair of electrodes relative to a subject and the controller is connected to control the at least one actuator.

67. The medical thermal ablation apparatus according to aspect 63 (or any other aspect herein) wherein the signal applicator comprises a plurality of pairs of coils and a selector circuit and the controller is configured to operate the selector circuit to apply an output of the heating energy signal generator to the coils of one of the pairs of coils at a time such that different ones of the pairs of coils are carrying the output signal from the heating energy signal generator at different times.

68. The medical thermal ablation apparatus according to aspect 63 (or any other aspect herein) wherein the signal applicator comprises at least one pair of coils and at least one actuator operable to move the at least one pair of coils relative to a subject and the controller is connected to control the at least one actuator.

69. Use of the apparatus according to any one of aspects 1 to 68 (or any other aspect herein) in the treatment of emphysema or COPD.

70. A method for controlling a medical thermal ablation apparatus, the apparatus useful for treatment of emphysema or COPD, the method comprising:

applying a signal from a heating energy signal generator across a pair of electromagnetic signal applicators, the electromagnetic signal applicators adapted to deliver electromagnetic energy to lung tissues for differential heating of diseased and healthier portions of the lung tissues, the pair of electromagnetic signal applicators comprising one electromagnetic signal applicator of a first set of two or more first electromagnetic signal applicators positionable on one side of a body to be treated and another electromagnetic signal applicator of a second set of at least one second electromagnetic signal applicators positionable on a second side of the body to be treated opposed to the first side;

at spaced apart times switching the signal so that the signal is applied across a different pair of the electromagnetic signal applicators, each different pair of the electromagnetic signal applicators comprising one of the first electromagnetic signal applicators and one of the second electromagnetic signal applicators.

71. The method according to aspect 70 (or any other aspect herein) wherein the electromagnetic signal applicators each comprises an electrode and the method comprises matching an impedance of the heating energy signal generator to an impedance presented by each pair of the electromagnetic signal applicators.

72. The method according to aspect 71 (or any other aspect herein) comprising storing settings for an impedance matching network in a data store and, in conjunction with switching the signal to apply the signal across the different pair of the electromagnetic signal applicators, configuring the impedance matching network according to one of the settings corresponding to the different pair of the electromagnetic signal applicators.

73. The method according to any one of aspects 70 to 72 (or any other aspect herein) wherein the electromagnetic signal applicators are flexible and the method comprises forming at least one of the electromagnetic signal applicators to conform to a concave surface.

74. The method according to aspect 73 (or any other aspect herein) wherein forming the one of the electromagnetic signal applicators comprises inflating a chamber adjacent to the one of the electromagnetic signal applicators.

75. The method according to any one of aspects 70 to 74 (or any other aspect herein) wherein switching the signal is performed at 100 Hz or less.

76. The method according to any one of aspects 70 to 75 (or any other aspect herein) wherein the signal comprises a radiofrequency (RF) signal.

77. The method according to aspect 76 (or any other aspect herein) wherein the RF signal has a frequency of at least 1 MHz.

78. The method according to aspect 76 (or any other aspect herein) wherein the RF signal has a frequency in the range of about 10 MHz to about 100 MHz.

79. The method according to any one of aspects 70 to 78 (or any other aspect herein) comprising regulating an output of the heating energy signal generator based at least in part on a temperature signal.

80. The method according to aspect 79 (or any other aspect herein) wherein regulating the output of the heating energy signal generator comprises applying a feedback control algorithm.

81. The method according to aspect 79 or 80 (or any other aspect herein) wherein the signal comprises a pulsed signal and regulating the output of the heating energy signal generator comprises applying time domain modulation to the pulsed signal.

82. The method according to aspect 81 (or any other aspect herein) wherein the time domain modulation comprises pulse width modulation.

83. The method according to any one of aspects 70 to 82 (or any other aspect herein) wherein the first and second sets of electromagnetic signal applicators each comprises a two dimensional array of electrodes.

84. The method according to aspect 83 (or any other aspect herein) wherein the two dimensional arrays of electrodes are shaped to conform generally to lungs of a human.

85. The method according to any one of aspects 70 to 84 (or any other aspect herein) comprising setting a controller to regulate the heating energy signal generator to raise a temperature at a location to a threshold temperature and to maintain the temperature at the threshold temperature or higher for a selected time period.

86. The method according to aspect 85 (or any other aspect herein) wherein the threshold temperature is at least 50° C.

87. The method according to any one of aspects 70 to 86 (or any other aspect herein) comprising setting the controller to regulate the heating energy signal generator to prevent the temperature at a location from exceeding a safe temperature threshold.

88. The method according to aspect 87 (or any other aspect herein) wherein the safe temperature threshold is lower than 50° C.

89. A method for treating a lung disease such as emphysema or COPD, the method comprising:

applying electromagnetic energy to tissues of a patient's lung between first and second electromagnetic signal applicators on opposing sides of the patient's lung;

continuing to apply the electromagnetic energy at a power level such that one or more areas of diseased tissue within the lung is heated to a temperature at least equal to a treatment temperature threshold while areas of healthier tissues of the lung are cooled by circulating blood such that temperatures of the areas of healthier tissues are .maintained below a safe temperature threshold that is lower than the treatment temperature threshold.

90. The method according to aspect 89 wherein the treatment temperature threshold is at least 50° C.

91. The method according to aspect 89 or 90 wherein applying the electromagnetic energy comprises matching an impedance of a source of the electromagnetic energy to an impedance presented by the first and second electromagnetic signal applicators.

92. The method according to any one of aspects 89 to 91 comprising changing an orientation of the patient relative to vertical during the method.

93. The method according to any one of aspects 89 to 92 comprising monitoring a temperature at a first location within the one or more areas of diseased tissue and controlling the application of the electromagnetic energy based on the monitored temperature of the first location.

94. The method according to any one of aspects 89 to 93 comprising monitoring a temperature at a second location within the one or more areas of healthier tissue and controlling the application of the electromagnetic energy based on the monitored temperature of the second location.

95. The method according to any one of aspects 89 to 94 comprising forming at least one of the electromagnetic signal applicators to conform to a concave surface of the patient.

96. The method according to aspect 95 wherein forming the electromagnetic signal applicator comprises inflating an inflatable chamber adjacent to the electromagnetic signal applicator.

97. The method according to any one of aspects 89 to 97 comprising flowing a liquid between the electromagnetic signal applicators and the patient while applying the electromagnetic energy.

98. The method according to aspect 97 wherein the liquid is electrically conductive.

99. The method according to aspect 98 wherein the liquid comprises a saline solution.

100. The method according to any one of aspects 89 to 99 comprising supplying chilled air for the patient to breathe while applying the electromagnetic energy.

101. The method according to any one of aspects 89 to 100 comprising actively cooling one or more of the electromagnetic signal applicators while applying the electromagnetic energy.

102. The method according to any one of aspects 89 to 101 comprising, while applying the electromagnetic energy changing a field direction of the electromagnetic energy.

103. The method according to aspect 102 wherein changing the field direction of the electromagnetic energy comprises moving the first and/or second electromagnetic signal applicators relative to the patient.

104. The method according to aspect 103 wherein moving the first and/or second electromagnetic signal applicators relative to the patient comprises moving the first and/or second electromagnetic signal applicators along a helical path relative to the patient.

105. The method according to aspect 102 wherein the first electromagnetic signal applicator is one of a first set of one or more electromagnetic signal applicators and the second electromagnetic signal applicators is one of a second set of two or more electromagnetic signal applicators and changing the field direction of the electromagnetic energy comprises switching to apply the electromagnetic energy between a pair made up of one of the first set of electromagnetic signal applicators and one of the second set of electromagnetic signal applicators other than the second electromagnetic signal applicator.

106. The method according to aspect 105 wherein the second set of electromagnetic signal applicators comprises an array of electromagnetic signal applicators that includes a first ow of the electromagnetic signal applicators spaced apart along the patient's body adjacent to a first one of the patient's lungs and a second column of the electromagnetic signal applicators spaced apart along the patient's body adjacent to a second one of the patient's lungs.

107. The method according to aspect 107 wherein the array of electromagnetic signal applicators comprises a plurality of columns of the electromagnetic signal applicators spaced apart along the patient's body adjacent to each one of the patient's lungs, each of the columns comprising a plurality of the electromagnetic signal applicators.

108. The method according to any of aspects 89 to 107 comprising while the one or more areas of diseased tissue within the lung is heated to a temperature at least equal to the treatment temperature threshold deflating the patient's lung and subsequently reflating the patient's lung.

109. The method according to any of aspects 89 to 108 wherein the electromagnetic signal applicators comprise electrodes and applying the electromagnetic energy to the tissues of the patient's lung comprises dielectric heating of the lung tissues.

110. The method according to aspect 109 comprising while applying the electromagnetic energy moving a shield located between one of the electrodes and the patient.

111. The method according to aspect 110 wherein the shield has a spatially varying electrical impedance.

112. The method according to any of aspects 89 to 108 wherein the electromagnetic signal applicators comprise coils and applying the electromagnetic energy to the tissues of the patient's lung comprises inductively coupling the energy to the tissues.

113. The method according to any one of aspects 89 to 112 wherein the electromagnetic energy comprises radiofrequency energy.

114. The method according to aspect 113 wherein the radiofrequency energy has a frequency of at least 1 MHz.

115. The method according to aspect 113 wherein the radiofrequency energy has a frequency in the range of about 10 MHz to about 100 MHz.

116. The method according to any one of aspects 89 to 115 comprising applying the electromagnetic energy to the entire lung of the patient.

117. Apparatus having any new and inventive feature, combination of features, or sub-combination of features as described anywhere herein.

118. Methods having any new and inventive steps, acts, combination of steps and/or acts or sub-combination of steps and/or acts as described anywhere herein.

BRIEF DESCRIPTION OF THE DRAWINGS

The accompanying drawings illustrate non-limiting example embodiments of the invention.

FIGS. 3A, 3B, 3C and 3D (collectively, FIG. 3) are cross sectional views of the patient's chest being exposed to an electromagnetic field, showing an alternative electrode arrangement.

FIG. 5A illustrates a deflated vest. FIG. 5B shows an inflated vest.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Methods and apparatus according to certain embodiments of the invention may be applied to selectively heat a diseased area of tissue in a patient while minimizing heating of other tissues in the patient. Heating may be achieved by exposing the diseased tissues to an electromagnetic field to cause dielectric or eddy current heating. The electromagnetic field may comprise radiofrequency (RF) energy. In some embodiments the RF energy comprises microwave radiation.

By application of electromagnetic energy, selected diseased tissues may be heated to temperatures above a threshold temperature. For example, diseased tissues may be heated to temperatures in the range of about 55 degrees C. to about 65 degrees C. The exact temperature to which diseased tissues are heated is often not critical. In many cases, heating to a slightly lower maximum temperature can be compensated for by maintaining the temperature for a longer duration. It is desirable to avoid heating of healthy tissues because overheating healthy tissues can damage the healthy tissues. The maximum temperature to which healthy tissue can be subjected without lasting damage is not known.

Certain embodiments of the invention are advantageously applied to treat diseased tissues that have reduced blood flow as compared to nearby healthier tissues. In such cases the diseased area(s) may be heated rapidly while the healthier tissues will be cooled by the blood flow and will therefore experience reduced increase in temperature as compared to the diseased tissues.

Emphysema is an example of a condition for which diseased area(s) have reduced blood flow. Certain embodiments of the invention can be particularly effective for treating emphysema because of the low mass (density) of the lungs and the high blood flow in healthy tissues within the lungs.

In some cases the diseased tissues are tissues in the lungs of a patient. For example, the patient may suffer from emphysema. For such treatments electromagnetic energy may be applied to heat diseased areas to temperatures of about 50 degrees C. or more. While this is done the temperatures of surrounding healthier lung tissue may be kept below a threshold temperature. The inventors estimate that healthy tissues in the lungs and organs in the vicinity of the lungs should not be subjected to temperatures in excess of about 40 degrees C. or about 45 degrees C.

Figure 1:
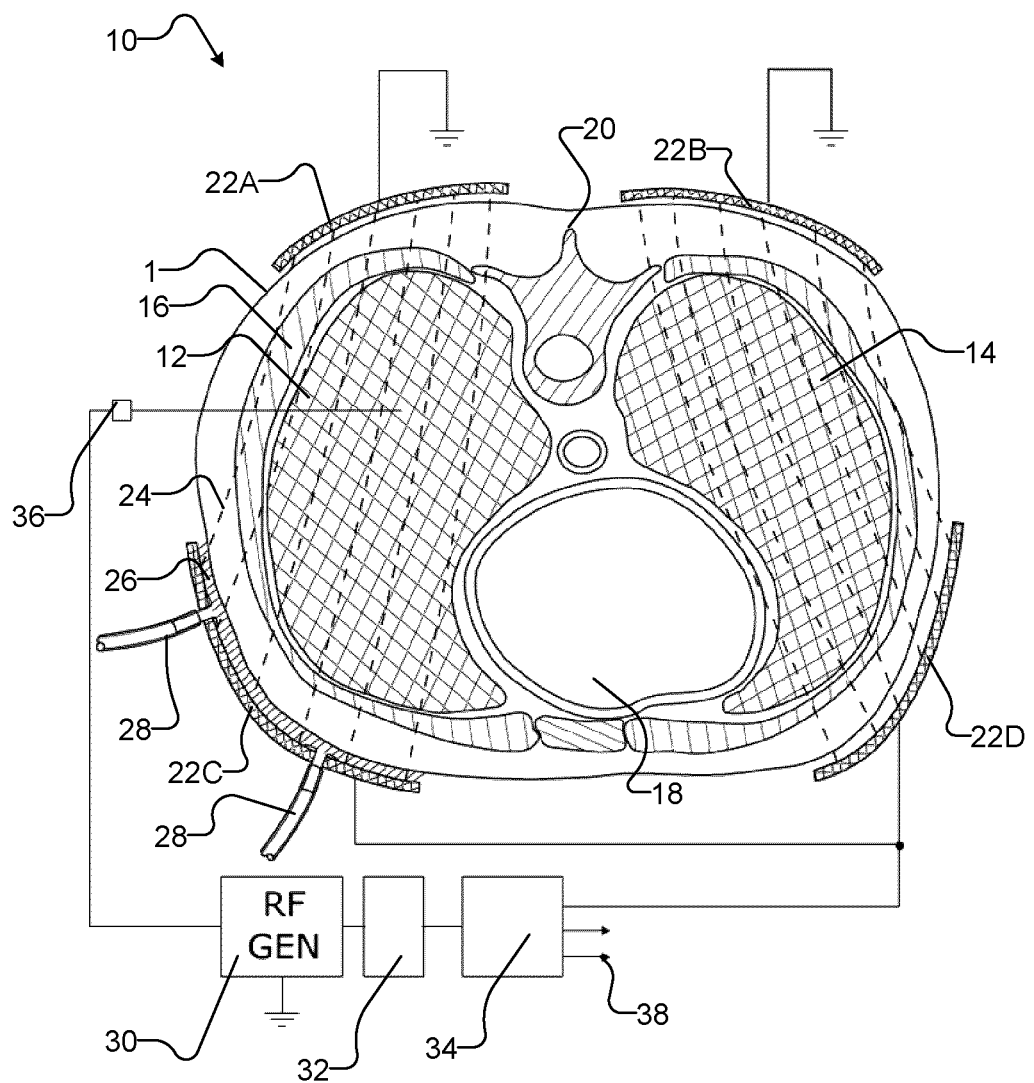
FIG. 1 is a cross section of a patient's chest being exposed to an electromagnetic field.

FIG. 1 illustrates apparatus 10 according to an example embodiment of the invention being applied to treat diseased tissues within lungs 12 and 14 of a patient P. Lungs 12 and 14 are surrounded by rib cage 16 inside the patient's body 1. To heat diseased tissues within lungs 12 and 14 while minimizing heat to adjacent organs like heart 18 and spine 20, a plurality of electrodes 22 (FIG. 1 shows four electrodes individually identified as 22A, 22B, 22C and 22D. In some embodiments apparatus 10 includes additional electrodes 22. The additional electrodes 22 may, for example be located on one or both sides of the plane of the cross-section of FIG. 1.

Electrodes 22 are dimensioned and placed to create an electric field 24 covering as much of lungs 12 and 14 as possible while minimizing penetration of electric field 24 into adjacent organs. Fortunately, the human anatomy allows such a placement.

To improve electrical coupling of electromagnetic energy to body 1 while cooling the surface of body 1, a saline solution 26 may optionally be introduced by tubes 28 between body 1 and electrodes 22. Such a liquid coupling can greatly improve the consistency of the coupling of the RF energy delivered by way of some or all of electrodes 22 into body 1. In alternative embodiments electrodes 22 comprise baths of electrically-conductive fluid such as, for example, saline solution. Saline solution 26 may, for example, comprise about 1 wt % NaCl in water. In some other embodiments an electrically-conductive gel is provided between electrodes 22 and body 1.

RF generator 30 supplies RF energy to electrodes 22 via an impedance matching network 32 and electrode selector circuit 34. The RF energy is applied between two or more of electrodes 22 via wires 36.

In some example embodiments the RF generator 30 has a maximum power output in the range of about 1 kW to about 5 kW. In some example embodiments, the RF energy output by RF generator 30 has a frequency or frequencies in the range of about 1 MHz to about 100 MHz or about 10 MHz to about 100 MHz.

It is optional but generally desirable to choose frequencies for electric field 24 in the industrial scientific and medical (ISM) bands of the spectrum. Such frequency choices may reduce or avoid interference between the RF energy generated by RF generator 30 and other signals such as communications signals. For example, RF generator 30 may have an output frequency of 13.56 MHz or 27 MHz.

Impedance matching network 32 is provided to match the output impedance of RF generator 30 to the impedance of body 1. This facilitates the efficient delivery of energy into body 1. Impedance matching networks are well known in the art.

In an example embodiment impedance matching network 32 may comprise an LC circuit such as a capacitor connected in series between one output terminal of RF generator 30 and electrode selector 38 followed by an inductor connected in parallel with electrode selector 38. The values of the capacitor and inductor may be determined after measuring the resistance and capacitance between pairs of electrodes 22 on body 1. For example, impedance matching network 34 may match a pure resistive impedance (e.g. 50 Ohms) of RF generator 30 to a complex impedance of a human or animal body.

Because the impedance presented by different patients may differ very significantly (e.g. the size of a patient can have a significant effect on the spacing of a pair of electrodes located on either side of a patient and whether or not a gel or conductive solution is provided can significantly affect impedance at the electrode-body interfaces) it can be desirable to provide an adjustable impedance matching network. The impedance matching network may be adjustable to provide a best matching of impedance for each of a plurality of electrode pairs.

In some embodiments the impedance matching network is self-adjusting (i.e. auto-tuning) to maximize delivery of power into the body. Technologies that can be used to auto-tune the matching network for optimal power delivery (based for example on measurements of reflected radiation) are described for example in: U.S. Pat. Nos. 5,364,392, 9,028,482 and 9,192,422 as well as other publications known to those of skill in the art.

To avoid resistive currents going through body 1, and for electrical safety, it is desirable to provide capacitive coupling between electrodes 22 and body 1. For example, one can coat electrodes 22 with a very thin layer of an insulating material. For example, a thin layer of Kapton™ tape may be applied between electrodes 22 and body 1.

Diseased tissues within one or both lungs 12, 14 may be heated by applying the output of RF generator 30 between two of electrodes 22 located on either side of the lung to be treated. Heating may be continued for sufficient time to raise the diseased tissues to temperatures above a threshold temperature for a time sufficient to achieve a desired treatment outcome.

In order to minimize heating of adjacent organs the direction of electromagnetic field 24 may be changed periodically. This may be achieved by applying the output of RF generator 30 between different pairs of electrodes 22. Different pairs of electrodes 22 may be selected such that the electric field changes direction but always passes through the portion(s) of lungs 12, 14 containing the diseased tissue to be treated. When this is done, the diseased lung tissues will be heated continuously while surrounding tissues will be heated only intermittently. In apparatus 10, electrode selector 38 switches the output of RF generator 30 to be applied between different pairs of electrodes 22. The switching frequency can be low. For example, electrode selector 38 may switch electrodes once every few seconds. In some non-limiting examples, electrode selector 38 switches electrodes to use a different pair of electrodes deliver of heating energy once every 30 to 300 seconds. In some non-limiting examples electrode selector 38 switches electrodes to use a different pair of electrodes at a frequency of 100 Hz or less.

In some cases the different pairs of electrodes 22 are selected such that a direction of alignment of the electric field within tissues of the patient is changed through an angle of at least 15 degrees (at least 10 degrees, at least 20 degrees and at least 25 degrees are also options) at least every few seconds (e.g. at least every 1 to 30 seconds). In some cases the different pairs of electrodes 22 are selected such that the direction of alignment of the electric field does not remain in the same plane for more than a few seconds. This may be facilitated by providing a two dimensional array of electrodes 22 adjacent each of the patient's lungs on at least one side of the patient.

Pairs of electrodes may be selected such that a volume of tissue (e.g. lung tissue) that includes diseased areas to be treated lies between electrodes of the selected pairs. By alternating applying heating energy using different ones of the selected pairs of electrodes the diseased areas within the volume of tissue may be heated consistently while surrounding tissues may be heated only some of the time. In some embodiments, for each lung, heating energy is delivered by way of one selected pair of electrodes at a time. In some embodiments delivery of heating energy is rotated among three or four or more selected pairs of electrodes. In such embodiments any one selected pair of electrodes may be active approximately 1/N of the time where N is the number of selected pairs of electrodes being used to apply heating energy to a particular lung or other volume of tissue.

In some embodiments an array of electrodes that substantially covers an area of a patient's lung is provided on a patient's chest and back. The electrode arrays may be mirror images of one another. Each of the electrode arrays may be shaped to conform to a shape of the patient's lung. In some embodiments each of the arrays is two dimensional and comprises plural columns each containing plural electrodes and plural rows each containing plural electrodes. In some embodiments such arrays are provided for one of a patient's lungs. In some embodiments such arrays are provided for both of a patient's lungs. Such arrays may be applied as described herein to deliver heating energy to tissues of either or both of the patient's lungs.

The electrodes of a pair of electrodes may be energized with opposite polarities. In some embodiments one electrode of a pair is grounded and the other electrode is connected to an output of RF signal generator 30. In some embodiments one electrode of a pair is connected to one output terminal of an RF signal generator and the other electrode is connected to another output terminal of the RF signal generator 30.

Healthier tissues of lungs 12, 14 may be protected from being heated to damaging temperatures by the fact that healthy lung tissue has much larger blood circulation than diseased tissue. When a non-contact heat source, such as radio-frequency (RF) energy, is directed at the lung the heat will be carried away from the healthy tissue by the blood flow while the diseased parts of the lung will heat up.

This works because the mass of the lungs is low (usually about 1 kg in an adult human) while blood flow through the lung is high (usually about 5 kg/minute or about 5 liters per minute in an adult human). The blood flow tends to equalize the temperature of healthy parts of the lung with the rest of the body which effectively acts as a heat-sink having a mass of tens of kilograms. This is 10 to 100 times larger than the effective heat sink mass for diseased portions of the lungs which is typically less than about one kilogram. When lungs are exposed to a form of energy causing heating, such as RF energy, the temperature rise of lung tissues will be inversely proportional to the effective heat-sinking mass. Therefore, diseased tissues that have poor blood circulation will be heated to temperatures significantly higher than healthier tissues that have normal blood circulation. Based on this, heating energy may be applied to cause the diseased areas of lung tissue to be heated to temperatures in the range of 50-70 degrees C. while healthy lung areas will only heat up a few degrees above normal body temperature.

To assist in keeping down the temperature of healthier parts of lungs 12, 14, patient P may be breathing chilled air during the procedure. The diseased parts of lungs 12, 14 will not get a sufficient amount of chilled air to keep them cool. Cooling may also be facilitated by means of an aerosol of liquefied air.

Methods as described herein may be implemented in ways that provide the advantage that the location(s) of diseased area(s) does not need to be precisely known in advance. Heating energy can be directed at the whole lung, but only the diseased areas will have their temperatures raised significantly.

Treatment methods as described herein may be applied to achieve various desired outcomes. For example, in some cases a single treatment in which a diseased tissue is heated to above a threshold temperature may be sufficient to achieve a desired outcome. For example, the desired outcome may be a reduction of the volume of diseased tissue. A single treatment may achieve sufficient volume reduction via fibrosis, ablation or other processes. In other cases the treatment may be repeated two or more times over the course of hours, days, weeks or months to achieved a desired reduction of volume of diseased tissues or other desired outcome.

Some embodiments optionally exploit the fact that when diseased lung tissue is heated to a temperature in the vicinity of about 60 degrees C. the diseased lung tissue may lose the ability to expand back after lungs are collapsed (pneumothorax). This may result from temperature-induced damage to the surfactant layer and other physiological reasons. A treatment method may comprise heating diseased lung tissue (e.g. tissue affected by COPD or emphysema) in a lung, collapsing the lung and then re-inflating the lung.

Heating the lung may be performed quickly (e.g. in seconds or minutes). Collapsing the lung may be performed by inserting a hypodermic needle into the pleural space and allowing air to leak into the pleural space. Supplying the lung with pure oxygen will speed up the collapse as it oxygen fully absorbed in the blood. The lung may be kept in a collapsed state for long enough to allow the diseased area(s) to collapse into a small volume. The lung may be re-inflated by evacuating the pleural space. This may be done, for example via the same needle used to collapse the lung. The procedure can be done on one lung at a time. The patient can breathe with the remaining lung. Collapsing and inflating lungs is done routinely in pulmonary medicine and need not be detailed here.

This treatment may cause the areas affected by emphysema to collapse and stay collapsed so that these areas are prevented from interfering with normal operation of the healthy parts of the lung. this may achieve results similar to those that can be achieved by surgically removing the diseased lung tissues without the risks of surgery. Other mechanisms may exist that do not require pneumothorax: the heated diseased area can lose volume through ablation, fibrosis or other mechanisms and allow healthy lung tissue to fill the voids.

The heating process may be performed open-loop (i.e. based on a previous experimental calibration of power and duration), or using sensing or closed loop control. In some embodiments apparatus 10 includes a controller that automatically controls one or more of: the power output of RF generator 30, the electrodes between which the output of RF generator 30 is applied, a duty cycle of RF generator 30 and a duration of a period during which RF generator 30 applies heating energy to a body 1 based at least in part on real time measurements of temperature(s) at one or more locations in tissues in a patient.

Temperature sensing may be performed using one or more sensors 36 placed in the patient's body and/or any suitable non-contact temperature sensing technology. In an example embodiment temperature of tissues within a patient is sensed using small temperature sensors such as thermistors, For example, a prototype embodiment used miniature glass encased thermistors such as Digikey™ part number 495-5820-ND to measure temperatures of lung tissues. Other example ways to measure temperatures of tissues include:

- hypodermic temperature sensors (these may for example comprise an electronic temperature sensor carried in a very fine gage needle (e.g. a needle about 0.6 mm in diameter);
- processing data obtained by a magnetic resonance imaging (MRI) system or other external imaging system capable of temperature monitoring;
- thermocouples;
- a bronchoscope equipped with a thermistor or other temperature sensor;
- solid-state temperature sensors;
- and the like.

A controller may implement any of various control algorithms. For example a controller of system 10 may implement a PID control loop. A controller may implement simple algorithms such as shutting off or reducing the power output of RF generator 30 when a desired temperature has been reached (e.g. a temperature in the range of about 55-65 degrees C.). In some embodiments the controller both modulates the power output of RF generator 30 as the temperature of a tissue is raised toward a desired temperature and shuts of delivery of power by RF generator 30 when the desired temperature has been reached. Feedback control can prevent the target temperature from being exceeded.

Embodiments that apply open-loop temperature control may optionally calculate a current temperature within a tissue of interest based on a mathematical model of the heat absorbed in the tissue and the cooling rate of the tissue. An output of the model may be applied to control power output of RF generator 30 and/or to stop RF generator 30 from further raising temperature of tissues after the model predicts that a threshold temperature has been reached.

In some embodiments one or more temperature sensors are applied to sense temperatures of non-targeted tissues. For example non-targeted organs identified as being likely to heat up the most, or as being the organs most sensitive to heat, may be identified and the temperatures within these organs may be monitored during treatment.

In an example embodiment a simple temperature sensor installed in a hypodermic needle provides accurate temperature measurements when the needle is inserted into the organ. A controller for apparatus 10 may be configured to discontinue treatment if a temperature of a non-targeted tissue exceeds a safe temperature threshold and/or to modulate application of heating energy from RF generator 30 if the temperature of the non-targeted tissue is rising toward or close to the safe temperature threshold.

Non-target temperature sensors which sense temperature of non-target tissues may be used on their own or combined with temperature sensors that measure temperature of targeted tissues. In some embodiments the same temperature sensor (e.g. an MRI-based temperature sensor or another non-contact temperature sensor) may monitor temperatures within both targeted tissues and non-targeted tissues.

Some embodiments modify the system described in U.S. Pat. No. 8,444,635 to include a temperature sensor, a controller connected to receive a temperature signal from the temperature sensor and configured to control delivery of radiation to heat tissues in a patient by a closed loop control algorithm.

In some cases it can be undesirable to place a temperature sensor in target tissues. For example, inserting a temperature sensor into certain areas of lung tissue could risk puncturing the lung. In some embodiments a model of the patient's anatomy may be used to estimate how temperature at a specific point in a targeted tissue and/or at a specific point in a non-targeted tissue relates to temperature at an alternative location in the patient. The alternative location may be selected to be a location at which a temperature sensor may be placed with lower risk and/or reduced adverse consequences. The other location may comprise one or more of muscle surrounding the lungs, exhaled air temperature, blood temperature at a certain location or the like.

A thermal model of the patient's anatomy may be generated from pre-operative images. Known thermal conductivities of different tissue types may be combined with known distributions of those tissue types in the patient, known geometries of electrodes, coils or other structures to be used to deliver heating energy to the tissues and a circulation model to estimate how temperatures at the alternative location(s) correlate to temperatures at the locations of interest. Temperatures measured at the alternative location(s) can then be used as proxies for temperatures at the locations of interest using the correlations determined using the model.

In some implementations the patient's orientation is taken into consideration. Lower parts of the lung typically contain more blood due to the effect of gravity than parts of the lung at higher elevations. This is called 'differential perfusion'.

The parts of the lung that contain the most blood can vary with patient orientation. The amount of blood at a location to be treated can affect the rate at which the temperature of tissue at that location increases when electromagnetic energy is delivered to the tissue.

In some embodiments a patient is moved into different postures (e.g. by rotating and/or tilting the patient and or rolling the patient over) as treatment is delivered. Apparatus according to some embodiments of the invention may provide a couch, chair, bed or other patient support that moves by tilting rotating or the like in coordination with the delivery of treatments. In some embodiments motions of the patient support are controlled by a controller that also controls application of heating energy to the patient.

Apparatus according to some embodiments provides instructions (e.g. on a display) to change the posture of the patient at selected points during a treatment.

Apparatus according to some embodiments estimates an effect of differential perfusion on properties of tissues in different parts of the lung (or other part of the anatomy). Such estimates may be based for example on information regarding the patient's anatomy (e.g. from pre-operative images). A profile for delivering energy to target tissues may take into account differential perfusion by increasing or decreasing the delivered energy depending on whether the target tissues are in a part of the lung at which the target tissues are expected to experience more rapid temperature rise as a result of differential perfusion (e.g. energy may be decreased where the target tissue is at a higher elevation and so the target tissue is depleted of blood) or the target tissues are expected to experience slower temperature rise as a result of differential perfusion (e.g. energy may be increased where the target tissue is at a lower elevation and so the target tissue contains a large amount of blood). Some embodiments of the apparatus provide a user interface that includes a control that a user may use to indicate a posture of the patient during a treatment. Compensation for differential perfusion may be based at least in part on the indicated posture.

It is generally desirable to apply electromagnetic energy to a patient's tissues such that the electric fields 24 within the tissues are generally uniform. Electric field 24 uniformity can be affected by various factors including:
  The sizes, shapes and positions of the electrodes;
  Impedance of the interface between the electrodes and the patient's body;
  The frequency or frequencies present in the electromagnetic energy being delivered by way of the electrodes;
  Where the electrodes are of different sizes, which electrode has the highest voltages applied to it (tissues near high voltage will tend to be heated to higher temperatures heat more quickly because the rate of heating relates to density of field lines).
Some embodiments manipulate one or more of these factors to achieve a desired electric field distribution in the patient. For example:
  electrodes may be constructed by choice of material and/or coating to have a spatially-varying resistivity.
  shields and/or waveguides may be interposed between the electrodes and the body of the patient.
  the electrodes (and/or shields and/or waveguides if present) may be moved as treatments are delivered.
Features such as one or more of the above may be applied, for example, to achieve a generally uniform distribution of electric field in a lung or other volume of tissue to be treated.

In some embodiments an arrangement of electrodes 22 is designed or customized using knowledge of a patient's anatomy and the geometry of the target tissues. For example, MRI and/or computed tomography CT images may be processed to identify regions of different consistency in the patient (e.g. fat tissue/muscle/bone). Working from known average electrical properties of these materials one can design a treatment plan that specifies one or more of:
  electrode arrangements;
  electrode switching sequence and/or timing;
  RF signal characteristics (power, frequency etc.);
The treatment plan may help to target the correct target tissue(s), achieve sufficiently uniform heating, and avoid excessive heating of critical tissue (heart, for example). In some embodiments an electrode pattern that comprises arrays of electrodes dimensioned to overlie a patient's lungs on two sides (e.g. chest and back) of a patient's body is generated by analysis of the patient's anatomy and a set of electrodes customized for the patient is fabricated by printing, cutting or other computer-controlled fabrication process using the electrode pattern.

Figure 2:
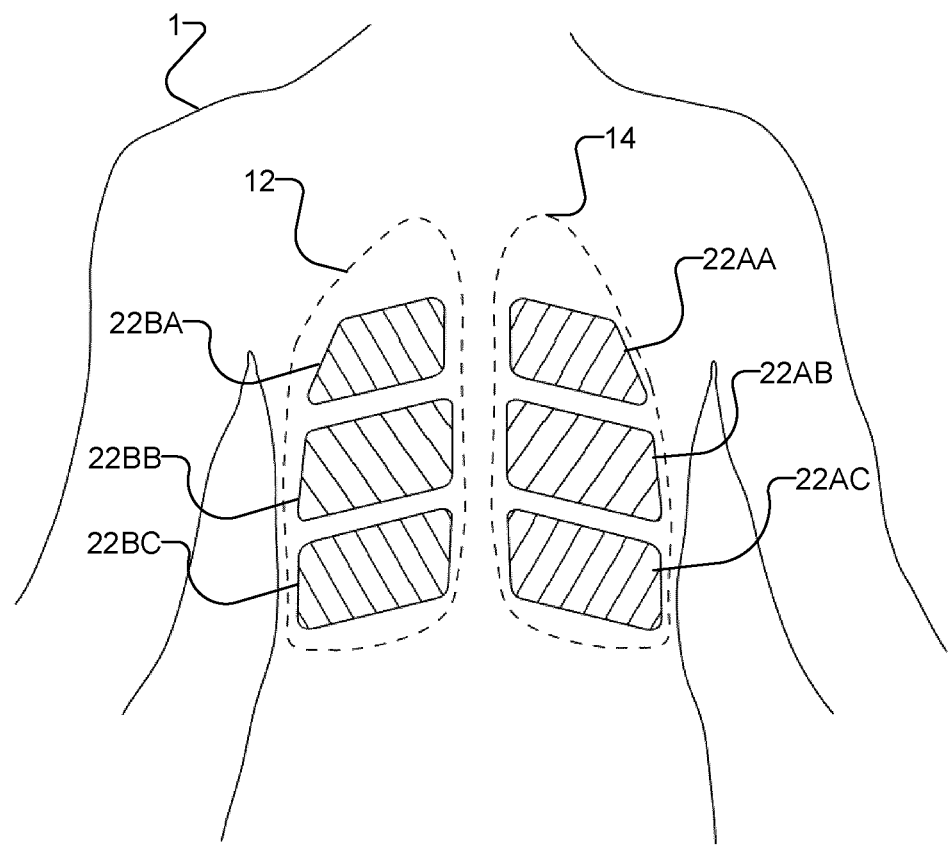
FIG. 2 is a view of the electrodes on the patient's back.

FIG. 2 shows an example arrangement of electrodes 22 on one side of a patient P (e.g. the patient's back) a similar arrangement of electrodes may be provided on an opposing side of the patient (e.g. the patient's chest). In this and some other embodiments a separate set of electrodes is provided overlying each of the patient's lungs. Here, electrodes 22AA through 22AC are provided over the patient's left lung and electrodes 22BA through 23BC are provided over the patient's right lung.

In this example, electromagnetic energy may be delivered to target lung tissues of the patient P by connecting the output of an RF generator 30 between a pair of electrodes 22 which includes one electrode on the patient's chest and another electrode on the patient's back. The pair of electrodes 22 may be directly opposed to one another in some cases and offset from one another in others.

The electrode arrangement of FIG. 2 may be varied in different ways including, for example:
  Replacing some or all of the illustrated electrodes with more electrodes, which may be smaller than the depicted electrodes in some cases.
  Dividing the illustrated electrodes to provide more columns of electrodes. The columns may, for example be arranged generally parallel to the patient's spine on one or both sides of the patient. For example, each of the illustrated electrodes 22 may be replaced by a row of two or three electrodes. An exemplary embodiment is shown in FIGS. 3A to 3D where each of the electrodes 22A, 22B, 22C, and 22D has been replaced by two electrodes.
  Dividing the illustrated electrodes to include more rows of electrodes.
An electrode selection circuit 34 as shown for example in FIG. 1 may apply heating energy (e.g. an output from an RF signal generator) to different ones of the electrode pairs at different times (electrode switching).

Figure 4:
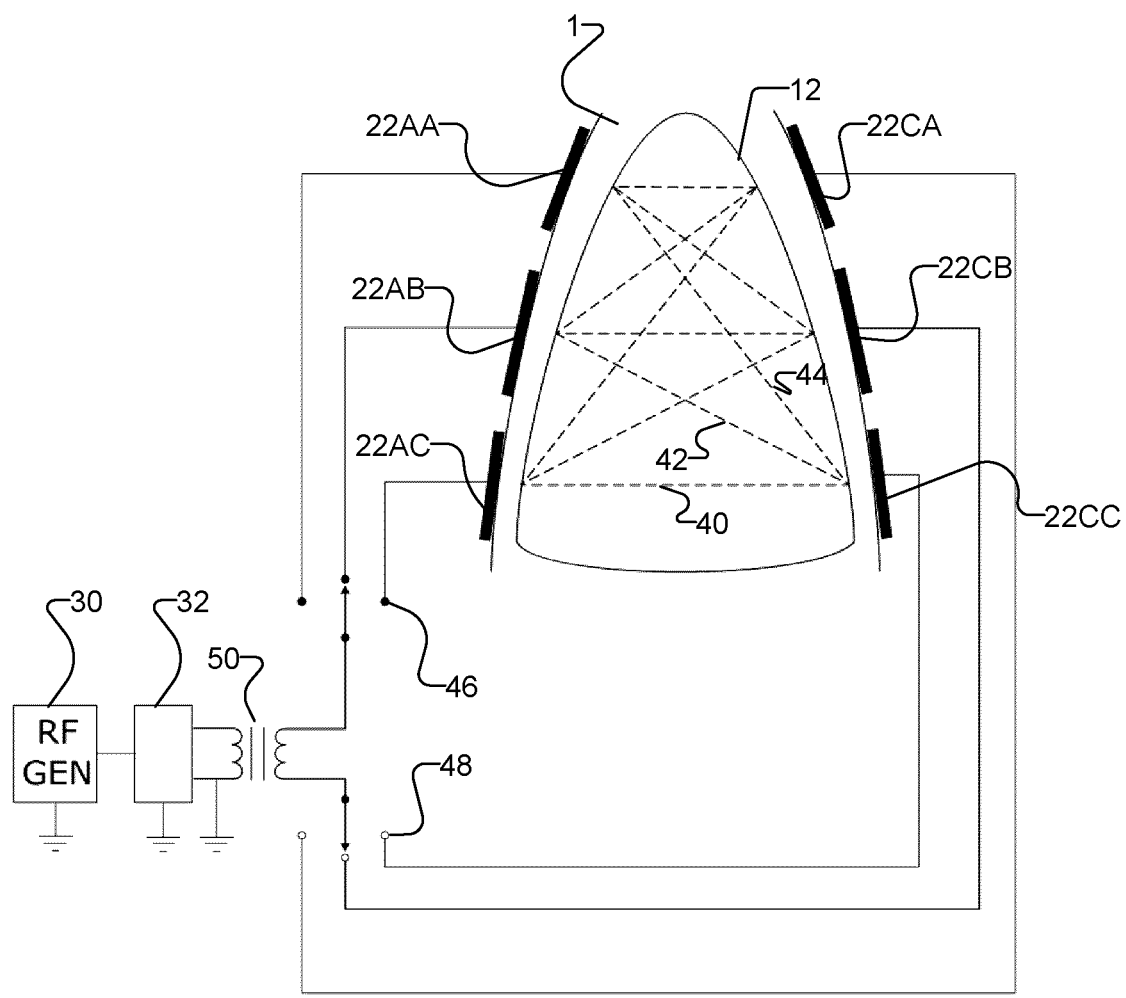
FIG. 4 is a side view of the patient, showing a method of electrode switching.

FIG. 4 illustrates an example of electrode switching. FIG. 4 is a side view of patient P in which electrodes 22AA through 22CC are shown. Electrodes 22CA through 22CC are on an opposite side of patient P from electrodes 22AA to 22AC. FIG. 4 shows that electrodes 22AA to 22CC provide 9 pairs of electrodes 22 wherein the electrodes of each pair include one electrode on one side of patient P and another electrode on an opposing side of patient P such that patient P is sandwiched between the electrodes of the pair.

The direction of an electric field 24 produced in patient P depends on which pair of electrodes 22 is being used to deliver heating energy. For example consider the three pairs of electrodes involving electrode 22CC. The electromagnetic field can be directed as shown by field lines 24, 25 and 26 by respectively pairing electrode 22CC with electrodes 22AA, 22AB and 22AC.

FIG. 4 shows an example situation in which electrode selection circuit 34 comprises electronically controlled switches or commutators 46 and 48. The impedance matching network may be constructed to provide a balanced output (balanced relative to ground potential) where a balanced configuration is desired. In the illustrated embodiment this is achieved by providing transformer 50.

Switches 46 and 48 may comprise, for example, electromechanical relays, electro-mechanical commutators, solid state switches such as RF FET transistors or RF relays or the like.

As shown in FIG. 4, different pairs of electrodes 22 may have electrode-to-electrode spacings that are significantly different. Some embodiments include mechanisms to compensate for different energy densities in body tissues that may result when heating energy is switched among different electrode pairs. Such compensation may, for example, take one or more of the following forms:

A controller may automatically set power output of RF generator 30 to different values depending on which pair of electrodes is being driven.

Some electrodes may be split into plural sections. Different ones of the sections or different combinations of the sections may be used depending on which other electrode the electrode is paired with.

Pulse width modulation or other time domain compensation may be applied depending on which pair of electrodes 22 is being driven.

A larger number of electrodes 22 may be provided such that more different pairs of electrodes 22 that produce similar energy densities when driven are available for selection.

An impedance matching network may be tuned or switched to match the impedance presented by different pairs of electrodes.

combinations of any two or more of the above.

etc.

Figure 5A:
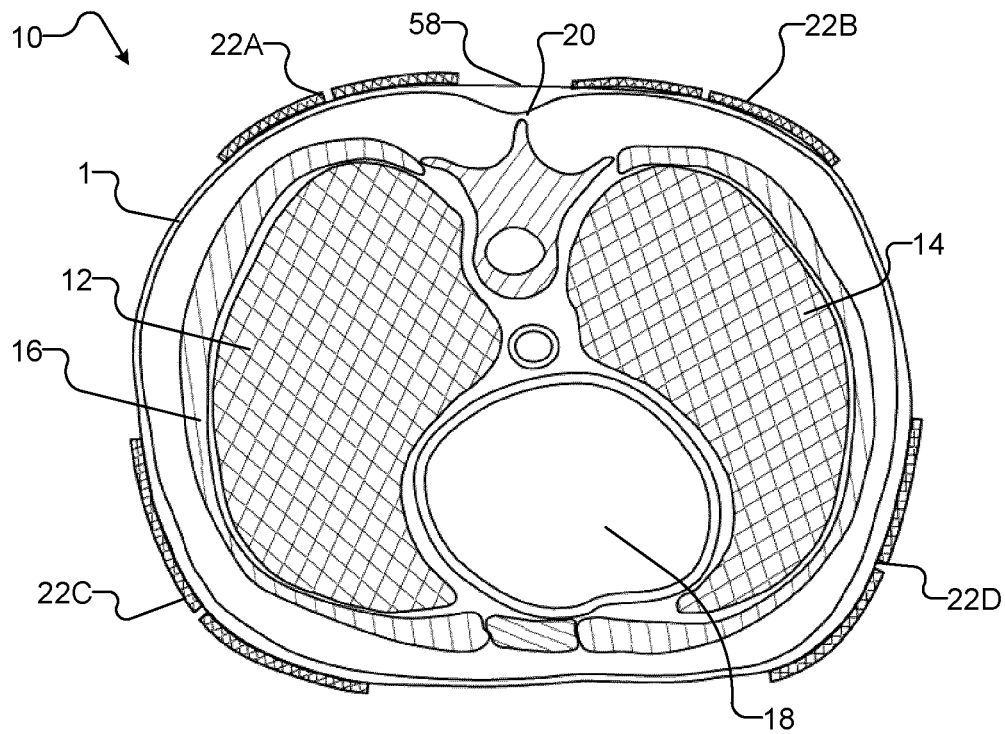
FIGS. 5A and 5B (collectively, FIG. 5) are cross sectional views of a patient's chest showing the electrodes being supported by an inflatable vest.
Figure 5B:
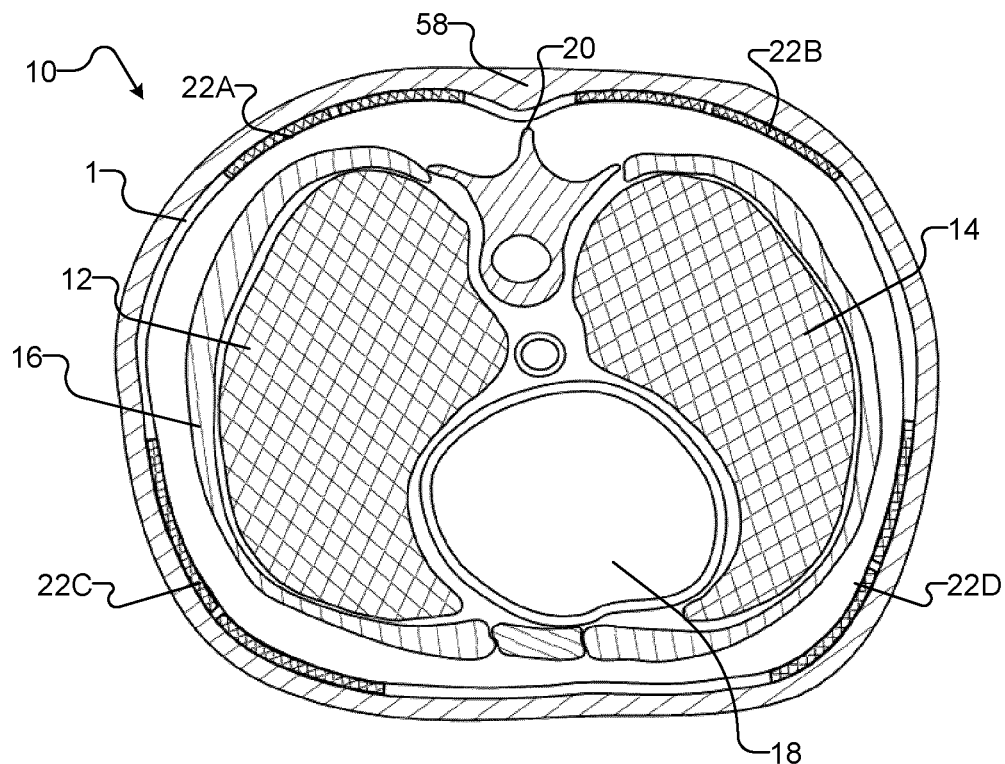

Electrodes 22 for use in applying heating energy to a patient may have any of a wide variety of forms including stick-on electrodes, electrodes mounted on a belt or the like, electrodes 22 supported by clothing such as a vest or the like. An exemplary vest 58 is shown in FIG. 5. Vest 58 may be inflatable. FIG. 5A shows vest 58 prior to inflation. FIG. 5B shows vest 58 that is inflated. In some embodiments some or all electrodes 22 comprise bladders containing an electrically-conductive liquid. Such electrodes can be advantageous where apparatus as described herein incorporates or is used in conjunction with a MRI system. During times when it is desired to deliver energy to the patients' tissues the bladders may be filled with the electrically-conductive fluid. During times when it is desired to obtain MRI information the electrically-conductive fluid may be withdrawn from the bladders.

Ideally the electrodes are provided in a way that simplifies applying the electrodes to the bodies of patients such that the electrodes are in close contact with the patients' bodies.

In some embodiments, some or all of electrodes 22 have one or more of the following features:

the electrodes are stretchable in length and/or width (for example, the electrodes may be made from an electrically-conductive stretchable fabric or a woven or non-woven conductive mesh or a sheet of a stretchable conductive plastic);

the electrodes are bendable;

the electrodes are attached to or are attachable to a vest, belt or other clothing article (for example using an adhesive or a hook and loop fabric coupling, or a clip, removable fastener, or the like);

the electrodes are designed to be made smaller, for example by cutting or tearing off to a size suitable for a particular patient;

the electrodes are made up of plural smaller electrodes, optionally connections between the smaller electrodes can be made or broken to adjust the sizes of the electrodes to suit individual patients.

Electrodes 22 may be held in place on a patient P, for example, by one or more of:

an adhesive (which may comprise a self-adhesive and/or a separately-applied adhesive) and/or gel;

an article of clothing to which the electrodes are attached or integrated into;

an article of clothing such as, for example, a stretchy and/or inflatable vest or shirt worn over top of the electrodes;

etc.

Where it is desirable to hold an electrode 22 against a part of a patient's body 1 that may be concave in form (e.g. the spine, areas around breasts etc.) a formed member such as a bendable support or inflatable chamber (which may be part of an inflatable article of clothing such as a vest) or the like may be provided to hold the electrode against the concave part of the patient's anatomy.

Where some or all electrodes 22 are provided on a support such as an article of clothing (e.g. a vest) or patient furniture such as a treatment couch, bed table or chair, the support may include passages in which a cool fluid is contained and/or circulating. The cool fluid may help to keep the patient cool. If the support is inflatable the passages containing the cool fluid may be the same as or different from chambers that can be pressurized to inflate the support. In some embodiments valves are provided such that circulation of the cool fluid may be inhibited in parts of the support that are in close proximity to a target tissue.

Figure 6:
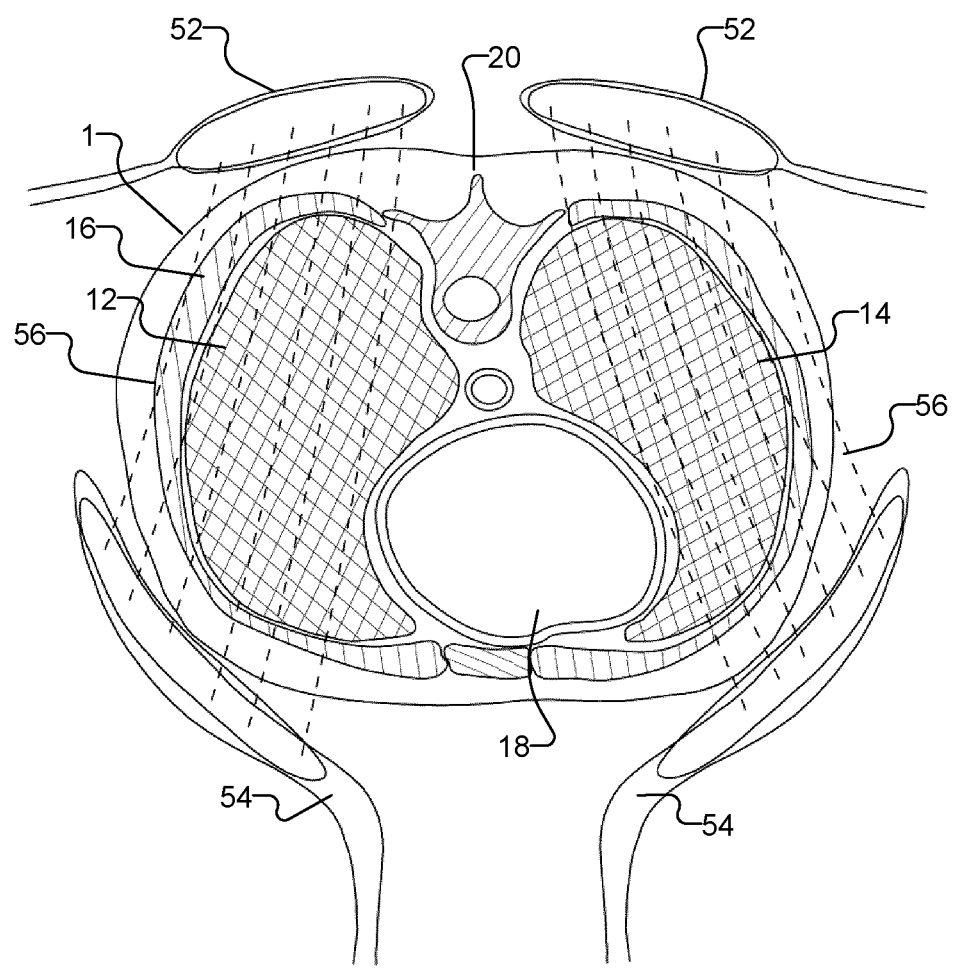
FIG. 6 is a cross section of a patient's chest being exposed to an electromagnetic field being generated by coils.

As described below, some embodiments provide coils instead of or in addition to electrodes. In such embodiments the coils may be supported against a patient in the same or similar ways as described above for electrodes. This is best illustrated in FIG. 6.

The innovations described herein may be applied in contexts which apply heating energy to body tissues in different ways. For example, electromagnetic energy can be coupled into a body to heat tissues by:

Placing at least one pair of electrodes on either side of the body such that at least a portion of the body is between the electrodes (effectively forming a capacitor in which the tissues of the body forms a dielectric) and deliver RF energy across the electrodes. Dielectric losses within the tissue will generate heat.

Place at least a part of the body inside a coil or sandwiched between several coils to form an inductor, drive a RF signal across the inductor and use the losses of this inductor (mainly eddy current losses) to generate heat in tissues of the body. Eddy current heating results where eddy currents in the patient's tissues are induced by a changing magnetic field.

Radiate electromagnetic energy into the body from an antenna, as disclosed for example in U.S. Pat. No. 8,444,635. Heating by radiating electromagnetic radiation into the body is mainly suitable for high frequencies such as microwave frequencies.

Closed-loop temperature control as described herein and/or switching the direction of electromagnetic field lines to reduce heating of non-targeted tissues may be provided in embodiments which apply any of these heating methods.

In order to control which areas are heated when using lower RF frequencies (e.g. 1 MHz to 100 MHz) the electrodes or coils that apply the RF energy to the body should be placed on opposing sides of the body. Placing electrodes or coils just on one side of the body will create uneven heating, with most heat generated near the electrodes or coils.

Various example embodiments are described herein in which electromagnetic energy is applied to a lung or other structure by way of electrodes. Other corresponding embodiments may be provided by replacing the electrodes with coils.

For eddy current and mainly magnetic field induced heating, electrodes can be replaced by RF coils, as shown in FIG. 6. The polarity of coils 52 and 54 is selected to create magnetic field lines 56 going through the lungs 12, 14. Multiple coils can be used in a coil switching arrangement similar to the electrode switching arrangements disclosed elsewhere herein. The magnetic field can be further directed by using ferrite blocks.

Figure 7A:
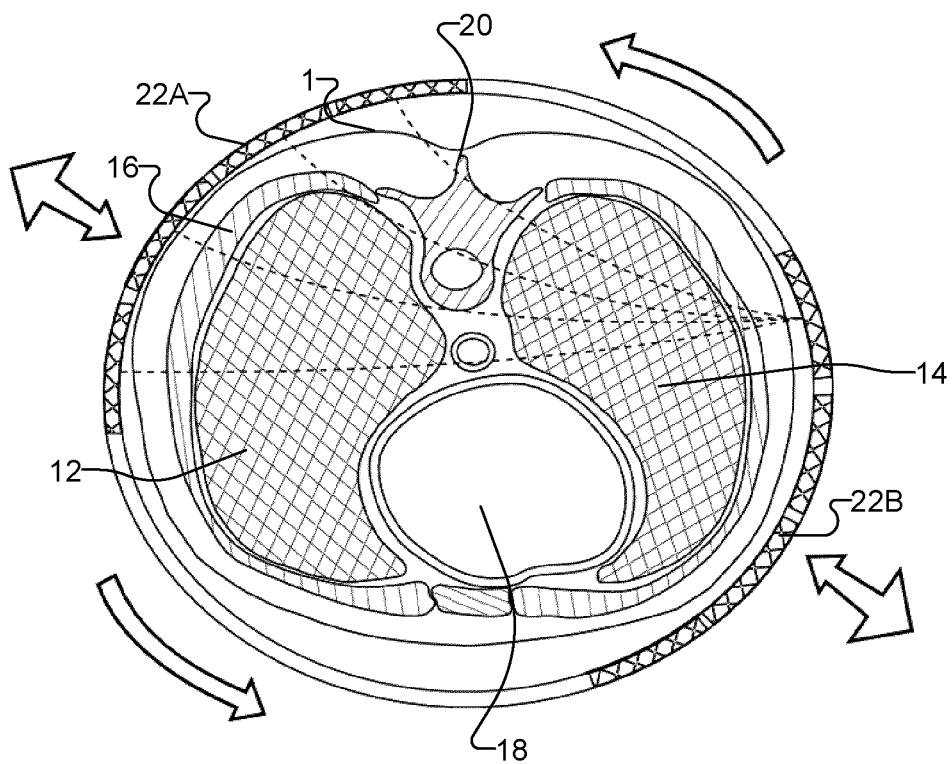
FIGS. 7A and 7B (collectively, FIG. 7) are cross sectional views of a patient's chest showing a pair of electrodes being actuated to move in a helical path around a patient's thorax as electromagnetic energy is being delivered.
Figure 7B:
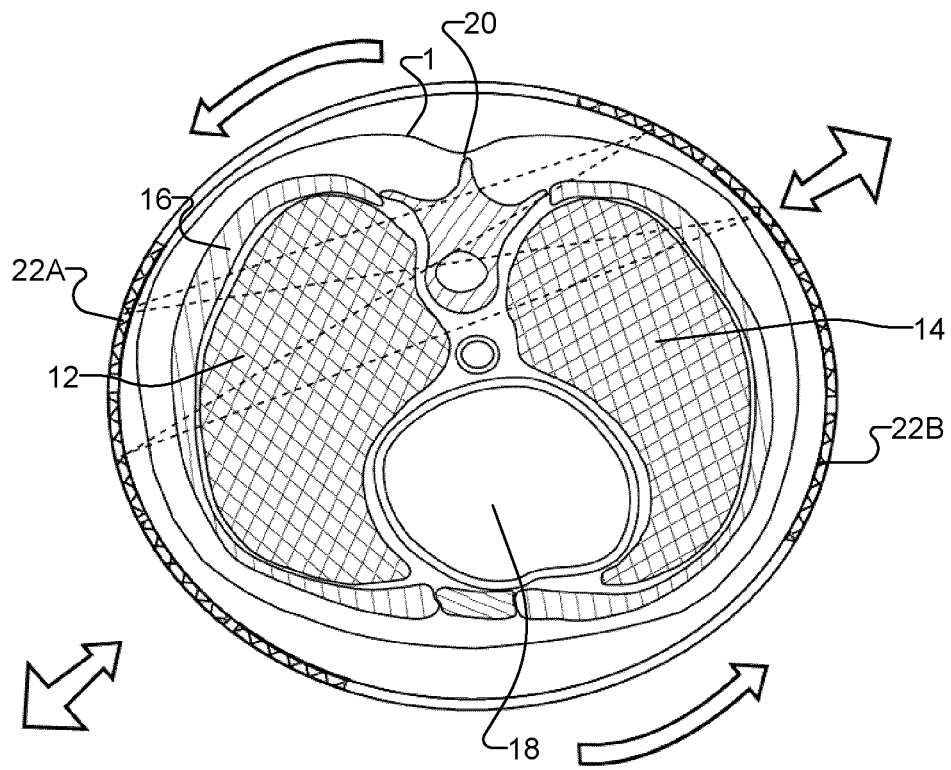
Figure 8:
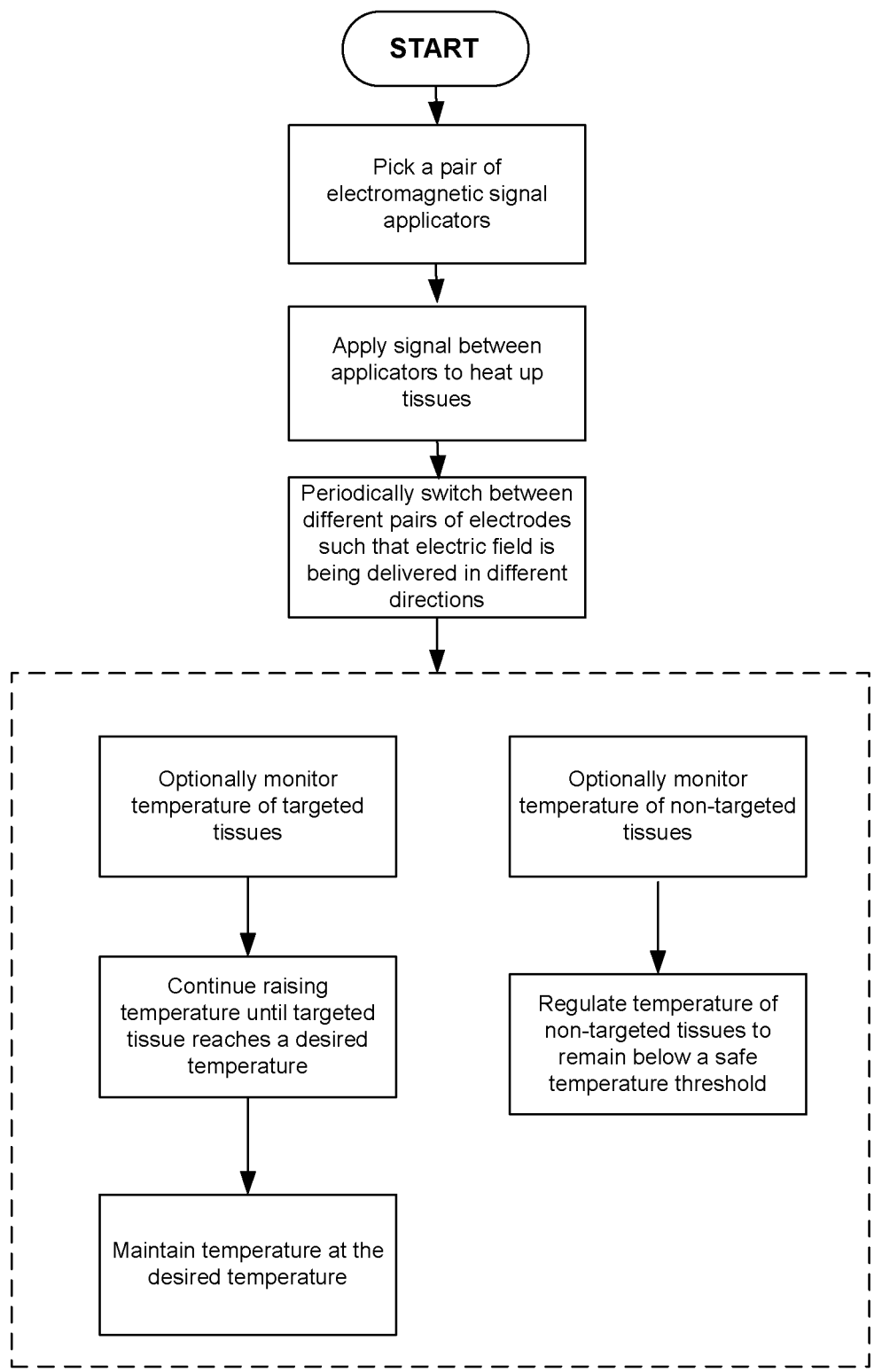
FIG. 8 is a flow chart showing an exemplary method of treating unwanted tissues in a patient.

Instead of providing fixed electrodes or coils apparatus may provide electrodes or coils that are movable relative to a patient P. For example: One or more pairs of electrodes may be carried on an actuator operative to move the pairs of electrodes relative to a patient. The pairs of electrodes may each include first and second electrodes that are respectively movable over first and second faces of the patient (e.g. chest and back of the patient). For example, one pair of electrodes 22 may be actuated to move in a helical path around a patient's thorax as electromagnetic energy is delivered by way of the electrodes 22, as shown in FIGS. 7A and 7B. As another example, one or more pairs of electrodes may be fixed in at least one dimension and the patient may be moved in the dimension relative to the fixed electrodes.

Apparatus according to some embodiments includes or is used in conjunction with a Faraday cage or shielded room to reduce electromagnetic interference with other equipment. In some embodiment, shielding is provided by a wire mesh cage made up of wires spaced apart by a few centimeters or less. The cage may be integrated into walls or other structures of a room.

EXAMPLE

A method as described herein was tested on rats. It was found out that miniature thermistors work well as direct temperature sensors while the thermocouples tested did not perform well. It is believed that the electric field interfered with the low level (under one mV), signals from thermocouples but not with the higher level (volts) signal from the thermistors. By the way of example, a suitable thermistor is model H1744 made by the U.S. Pat. No. Sensor company (http://www.ussensor.com/). This thermistor has an outside diameter of 0.43 mm.

The system was tested on several rats with induced emphysema in one of the lungs. The parameters used were:
  RF power of 100 W at 13.56 MHz.
  Series C parallel L matching network with saline irrigated electrodes.
  Reflected power was under 5%. Each electrode was approximately 25×50 mm, coated with 25 μm thick Kapton™ tape. The tape does not attenuate the capacitive currents much because it is very thin, therefore allowing high capacitance between electrode and the body. Rats were shaved in the areas of contact with the electrodes.

Heating time was about 100 seconds. The healthy lung reached about 41 degrees C., while the areas with emphysema reached about 55 degrees C. All rats survived the treatment. Subsequent autopsy verified scar tissue in the areas of induced emphysema.

In the tests conducted on rats the dielectric heating was more effective than the magnetic field induced heating, but there may be unique benefits to each one of them.

Interpretation of Terms

Unless the context clearly requires otherwise, throughout the description and the claims:
  "comprise", "comprising", and the like are to be construed in an inclusive sense, as opposed to an exclusive or exhaustive sense; that is to say, in the sense of "including, but not limited to";
  "connected", "coupled", or any variant thereof, means any connection or coupling, either direct or indirect, between two or more elements; the coupling or connection between the elements can be physical, logical, or a combination thereof;
  "herein", "above", "below", and words of similar import, when used to describe this specification, shall refer to this specification as a whole, and not to any particular portions of this specification;
  "or", in reference to a list of two or more items, covers all of the following interpretations of the word: any of the items in the list, all of the items in the list, and any combination of the items in the list;
  the singular forms "a", "an", and "the" also include the meaning of any appropriate plural forms.
  "electromagnetic signal applicator" is a generic term that encompasses electrodes (e.g. which may be used to apply electric fields for dielectric heating), coils, (e.g. which may be used to apply magnetic fields for eddy current heating, and antennas (e.g. which may be used to apply microwaves to heat tissues).

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Certain embodiments of the invention incorporate control systems or controllers. Such controllers or control systems may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

Software and other modules may reside on servers, workstations, personal computers, tablet computers, embedded controllers, process controllers and other devices suitable for the purposes described herein.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. an electrode, oscillator, switch, controller, temperature sensor, software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Methods according to the examples described herein may be varied. For example, while elements are at times shown as being performed sequentially, they may instead be performed simultaneously or in different sequences.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. Medical thermal ablation apparatus useful for treatment of emphysema or COPD, the apparatus comprising:
a plurality of electromagnetic signal applicators, the plurality of electromagnetic signal applicators adapted to deliver electromagnetic energy to lung tissues for differential heating of diseased and healthier portions of the lung tissues, the plurality of electromagnetic signal applicators comprising a first set of two or more first electromagnetic signal applicators positionable on one side of a body to be treated and a second set of at least one second electromagnetic signal applicators positionable on a second side of the body to be treated opposed to the first side such that the body is between the first and second electromagnetic signal applicators;
a heating energy signal generator; and
a selector circuit connected to receive an output signal from the heating energy signal generator and operative to selectively apply the output signal between a selected one or more of the first electromagnetic signal applicators and a selected one or more of the second electromagnetic signal applicators and to switch from applying the output signal between the currently selected first and second electromagnetic signal applicators to between a different selected combination of one or more of the first electromagnetic signal applicators and one or more of the second electromagnetic signal applicators at spaced apart times;
wherein at least one of the first and second electromagnetic signal applicators is stationary and the apparatus comprises a controller and an actuator controlled by the controller and operable to move the body relative to the at least one of the first and second electromagnetic signal applicators.

2. The medical thermal ablation apparatus according to claim 1 wherein the electromagnetic signal applicators each comprises an electrode.

3. The medical thermal ablation apparatus according to claim 2 comprising an impedance matching network between the heating energy signal generator and the electrodes and the controller wherein the impedance matching network comprises a plurality of settings, each of the settings provides impedance matching for at least one of a plurality of pairs of the electrodes, each of the pairs of electrodes correspond to one of the settings and the controller is connected to control the impedance matching network to switch the impedance matching network to the setting corresponding to a currently selected one of the pairs of electrodes.

4. The medical thermal ablation apparatus according to claim 2 wherein the apparatus comprises a source of a fluid connected to supply the fluid to outlets at the electrodes.

5. The medical thermal ablation apparatus according to claim 2 wherein at least some of the electrodes comprise bladders connected to a supply of a fluid and the apparatus comprises one or more pumps connected to evacuate the fluid and the controller is configured to operate the one or more pumps to evacuate the fluid from one or more of the bladders, when the fluid has been evacuated from the one or more bladders operate a MRI machine to acquire MRI data from the body.

6. The medical thermal ablation apparatus according to claim 1 wherein the heat energy signal generator has first and second outputs and one of the first and second outputs of the heat energy signal generator is grounded and the selector circuit is configured to selectively connect the first output to the selected one or more of the first electromagnetic signal applicators and to selectively connect the second output to the a selected one or more of the second electromagnetic signal applicators.

7. The medical thermal ablation apparatus according to claim 1 wherein the heating energy signal generator comprises a radiofrequency (RF) signal generator.

8. The medical thermal ablation apparatus according to claim 7 wherein the RF signal generator is operable to output a signal having a frequency in an ISM band in the range of about 1 MHz to about 100 MHz.

9. The medical thermal ablation apparatus according to claim 1 wherein the controller is connected to receive a signal indicative of a temperature of tissue at one or more locations within the body and configured to apply feedback control to regulate heating energy delivered into the body from the heat energy signal generator based at least in part on the temperature signal.

10. The medical thermal ablation apparatus according to claim 9 further comprising a subcutaneous and/or invasive temperature sensor wherein the temperature signal comprises an output signal from the subcutaneous and/or invasive temperature sensor.

11. The medical thermal ablation apparatus according to claim 9 wherein the controller comprises a thermal model of at least a portion of the body, the thermal model correlating temperature at one of the locations to temperature of a location of interest and the controller is configured to apply the thermal model using the temperature signal as an input and to regulate the heating energy based at least in part on an output of the thermal model.

12. The medical thermal ablation apparatus according to claim 9 wherein the temperature signal is derived from an external system capable of temperature monitoring.

13. The medical thermal ablation apparatus according to claim 9 wherein the temperature signal comprises a signal derived from processing a magnetic resonance imaging (MRI) signal.

14. The medical thermal ablation apparatus according to claim 9 wherein the controller is configured to regulate the heating energy to raise a temperature at one of the one or more locations to a temperature of at least 50 C and to maintain the temperature at 50 C or higher for a selected time period.

15. The medical thermal ablation apparatus according to claim 9 wherein the controller is configured to regulate the heating energy to prevent the temperature at one of the one or more locations from exceeding a safe temperature threshold.

16. The medical thermal ablation apparatus according to claim 1 wherein the controller is configured to perform one or more of: controlling a power of the output signal; applying time domain modulation to the output signal; and controlling the heat energy signal generator to emit the output signal as a pulsed signal wherein the controller is configured to control widths of the pulses.

17. The medical thermal ablation apparatus according to claim 2 wherein the electrodes of at least one of the first and second sets of electromagnetic signal applicators are arranged in a two-dimensional array.

18. The medical thermal ablation apparatus according to claim 1 wherein the first and second sets of electromagnetic signal applicators respectively comprise first and second two-dimensional arrays of electrodes wherein each electrode of the first array of electrodes is positioned opposite a corresponding electrode of the second array of electrodes.

19. The medical thermal ablation apparatus according to claim 1 wherein the electromagnetic signal applicators each comprises a coil.

20. Medical thermal ablation apparatus useful for treatment of emphysema or COPD, the apparatus comprising:
a plurality of electromagnetic signal applicators, the plurality of electromagnetic signal applicators adapted to deliver electromagnetic energy to lung tissues for differential heating of diseased and healthier portions of the lung tissues, the plurality of electromagnetic signal applicators comprising a first set of two or more first electromagnetic signal applicators positionable on one side of a body to be treated and a second set of at least one second electromagnetic signal applicators positionable on a second side of the body to be treated opposed to the first side such that the body is between the first and second electromagnetic signal applicators;
a heating energy signal generator;
a selector circuit connected to receive an output signal from the heating energy signal generator and operative to selectively apply the output signal between a selected one or more of the first electromagnetic signal applicators and a selected one or more of the second electromagnetic signal applicators and to switch from applying the output signal between the currently selected first and second electromagnetic signal applicators to between a different selected combination of one or more of the first electromagnetic signal applicators and one or more of the second electromagnetic signal applicators at spaced apart times; and
bias means for biasing one or more of the electromagnetic signal applicators toward the body wherein: the bias means comprises an inflatable chamber and a source of a pressurized cool fluid in fluid communication with the inflatable chamber; and the one or more of the electromagnetic signal applicators is flexible and the bias means is adapted to flex the one or more of the electromagnetic signal applicators to conform to a concave surface.

* * * * *